(12) United States Patent
Sganga et al.

(10) Patent No.: US 12,296,117 B2
(45) Date of Patent: May 13, 2025

(54) IMAGE SPACE CONTROLLED MANUAL CATHETER

(71) Applicant: Remedy Robotics, Inc., San Francisco, CA (US)

(72) Inventors: Jake Anthony Sganga, San Francisco, CA (US); David James Bell, Mill Valley, CA (US)

(73) Assignee: REMEDY ROBOTICS, INC., San Francisco, CA (US)

( * ) Notice: Subject to any disclaimer, the term of this patent is extended or adjusted under 35 U.S.C. 154(b) by 0 days.

(21) Appl. No.: 18/806,404

(22) Filed: Aug. 15, 2024

(65) Prior Publication Data
US 2025/0058086 A1  Feb. 20, 2025

Related U.S. Application Data

(60) Provisional application No. 63/519,924, filed on Aug. 16, 2023.

(51) Int. Cl.
*A61M 25/01* (2006.01)
(52) U.S. Cl.
CPC .... *A61M 25/0136* (2013.01); *A61M 25/0147* (2013.01); *A61M 2205/50* (2013.01)
(58) Field of Classification Search
CPC .......... A61M 25/0136; A61M 25/0147; A61M 2205/50
See application file for complete search history.

(56) References Cited

U.S. PATENT DOCUMENTS

| 7,756,563 | B2 | 7/2010 | Higgins |
|---|---|---|---|
| 9,727,963 | B2 | 8/2017 | Mintz |
| 11,690,683 | B2 | 7/2023 | Bell |
| 11,857,156 | B2 | 1/2024 | Roelle |
| 2005/0203382 | A1 | 9/2005 | Govari |
| 2006/0074383 | A1 | 4/2006 | Boulais |
| 2007/0265503 | A1 | 11/2007 | Schlesinger |
| 2008/0255505 | A1 | 10/2008 | Carlson |
| 2011/0106101 | A1 | 5/2011 | Tortonese |
| 2011/0218536 | A1 | 9/2011 | Wunderlich |
| 2011/0319714 | A1 | 12/2011 | Roelle |

(Continued)

OTHER PUBLICATIONS

International Search Report for International Application No. PCT/US2024/042503 dated Dec. 10, 2024.

*Primary Examiner* — Joel M Attey
*Assistant Examiner* — John A Doubrava
(74) *Attorney, Agent, or Firm* — Knobbe Martens Olson & Bear LLP

(57) ABSTRACT

A steerable catheter system is disclosed. The system includes a steerable catheter including a handle and a steerable elongated body. The handle includes user inputs for image space control commands for articulating the elongated body with respect to a plane of a medical image. The elongated body includes pose determination features that allow determination of a roll angle of the elongated body. The system also includes a control unit that receives the image space control commands, determines the roll angle of the elongated body based on the pose determination features, translates the image space control commands into pullwire commands based on the roll angle, and transmits the pullwire commands to the steerable catheter, whereby the elongated body is articulated according to the pullwire commands.

8 Claims, 21 Drawing Sheets

(56) References Cited

U.S. PATENT DOCUMENTS

| | | |
|---|---|---|
| 2012/0069167 A1 | 3/2012 | Liu |
| 2013/0096377 A1 | 4/2013 | Duindam |
| 2014/0114180 A1 | 4/2014 | Jain |
| 2015/0142013 A1 | 5/2015 | Tanner |
| 2018/0071487 A1 | 3/2018 | Khuu et al. |
| 2018/0125591 A1 | 5/2018 | Camarillo |
| 2020/0297444 A1* | 9/2020 | Camarillo .............. G16H 30/40 |
| 2020/0405397 A1* | 12/2020 | Liu ........................ A61B 34/10 |
| 2021/0338355 A1 | 11/2021 | Yip |
| 2021/0393333 A1 | 12/2021 | Sganga |
| 2021/0393335 A1 | 12/2021 | Sganga |
| 2021/0393336 A1 | 12/2021 | Sganga |
| 2022/0142464 A1* | 5/2022 | Petroff ................. A61B 1/0676 |
| 2023/0000563 A1 | 1/2023 | Bell |
| 2023/0000566 A1 | 1/2023 | Bell et al. |
| 2023/0128303 A1 | 4/2023 | Ouyang |
| 2023/0240513 A1* | 8/2023 | Shia ........................ A61B 1/05 |
| | | 600/104 |

* cited by examiner

IMAGE SPACE CONTROLLED MANUAL CATHETER

PRIORITY APPLICATION

This application claims priority to U.S. Provisional Application No. 63/519,924, filed Aug. 16, 2023, which is incorporated herein by reference. Any and all applications for which a foreign or domestic priority claim is identified in the Application Data Sheet as filed with the present application are hereby incorporated by reference under 37 CFR 1.57.

BACKGROUND

Field

The present application is directed to intraluminal tools or medical instruments, such as catheters.

Description

Endovascular medical procedures are common. During an endovascular procedure, a tool or medical instrument that is generally configured as a long, thin, flexible body is inserted into and navigated through a lumen or other cavity of the body.

In some instances, the tools or medical instruments are articulable or controllable, for example, using one or more pull wires, to allow an operator to navigate the tool or medical instrument within the body. Such navigation is often accomplished through deflection (for example, bending) of the distal tip of the tool or medical instrument.

Some tools or medical instruments are configured for manual control, for example, using knobs or levers mounted on a proximally located handle of the tool or medical instrument. In other instances, the tools or medical instruments can be configured for robotic control, for example, control by a robotic medical system. In some embodiments, an operator can use the robotic medical system (for example, a controller, user interface, and/or the like) to robotically control the tool or medical instrument.

SUMMARY

This application describes devices, systems, and methods for controlling intraluminal tools during a medical procedure. In some embodiments, control inputs on a manually controllable catheter (e.g., a handheld or a hand operated catheter) are provided with respect to a plane of a two-dimensional medical image such as an X-ray. For example, control inputs can be provided to adjust a heading of an instrument within the plane of the medical image and/or to adjust an incline of the instrument into or out of the plane of the medical image. The control inputs can be provided via inputs on a handle or base of the catheter. Providing a control scheme in which control inputs are provided by a user with respect to the plane of the medical image can advantageously facilitate intuitive and natural control of the instrument. In some instances, such a control scheme is referred to herein as "image space control" because control inputs are provided with respect to the plane of a two-dimensional medical image.

Articulating the instrument, either to adjust the heading of the instrument within the two-dimensional plane of the medical image or to adjust the incline of the instrument into or out of the plane of the medical image, typically requires an accurate understanding of the current roll angle of the instrument about its longitudinal axis. During a medical procedure it can be difficult for a human user controlling the instrument to keep track of or understand the current roll of the instrument, especially as the instrument is navigated through generally tortuous paths, such as luminal networks of the body. As described in this application, in some instances, a user can operate the manually controllable catheter without regard for the current roll of the instrument. That is, the user can provide control inputs in image space (e.g., relative to the plane of the image) and a computer system can translate those image space control inputs into appropriate pullwire or articulation commands based on a roll estimate determined by the system.

In a first aspect, a manually-controlled steerable catheter configured for image space control, includes a handle configured to be held by a hand of a user, the handle comprising one or more manually operated user inputs, wherein the user inputs are configured to be allow a user to provide an in-plane input command to adjust a heading of the steerable catheter within a plane of a medical image, and an out-of-plane input command to adjust an incline of the steerable catheter into or out of the plane of the medical image. The handle also includes one or more spools, one or more motors, each of the one or more motors coupled to one of the one or more spools to cause rotation thereof, a motor controller configured to control the one or more motors, and a communications module configured to communicate the in-plane input command and the out-of-plane input command to a control unit that translates the in-plane input command and the out-of-plane input command into pullwire commands, and to communicate the pullwire commands to the motor controller. The steerable catheter also includes an elongated body extending from the handle, the elongated body configured for insertion into a lumen of a patient. the elongated body includes a plurality of pullwires configured to allow deflection of a distal portion of the elongated body, wherein the pullwires extend along or through the elongated body and are engaged with the one or more spools, and one or more pose determination features positioned on the elongated body and configured to allow for determination of at least a roll angle of the distal portion of the elongated body.

The steerable catheter can include one or more of the following features in any combination: (a) wherein the plurality of pullwires comprise four pullwires configured to allow deflection of the distal portion of the elongated body in four orthogonal directions; (b) wherein the pose determination features comprise one or more radio-opaque fiducials positioned on the distal portion of the elongated body, wherein the one or more radio-opaque fiducials are configured such that the roll angle of the distal portion of the elongated body can be determined from the two-dimensional appearance of the one or more radio-opaque fiducials in a medical image that includes a view of the distal portion of the elongated body; (c) wherein the medical image comprises an x-ray image; (d) wherein the user inputs comprise one or more of a button or a joystick positioned on the handle; (e) a disposable portion comprising a first portion of the handle comprising the one or more spools, and the elongated body; and a reusable portion comprising a second portion of the handle comprising the one or more user inputs, the one or more motors, the motor controller, and the communications module; (f) wherein the disposable portion is configured to selectively couple with the reusable portion; (g) wherein: the first portion of the handle comprises one or more first gear interfaces coupled with the one or more spools; and the second portion of the handle comprises one or more second gear interfaces coupled with the one or more motors; (h) wherein, when the disposable portion is selectively coupled with the reusable portion, the one or more first gear interfaces couple with the one or more second gear interfaces to couple the one or more motors to the one or more spools; (i) wherein the reusable portion is sterilizable; (j) a lumen extending through the elongated body; (k) wherein the handle further comprises a contrast injection user input, operable by a user to control contrast injection; (l) wherein the one or more pose determination features comprise one or more of: an electromagnetic sensor or a Fiber Bragg grating sensor; and/or other features as described herein.

In another aspect, a manually-controlled steerable catheter system configured for image space control includes a manually-controlled steerable catheter comprising a handle configured to be held by a hand of a user, and a steerable elongated body extending from the handle and configured for insertion into a lumen of a patient. The handle comprises one or more user inputs configured to allow a user to provide image space control commands for articulating the elongated body with respect to a plane of a medical image that includes a view of a distal portion of the elongated body. The elongated body comprises one or more pose determination features configured to allow determination of at least a roll angle of the distal portion of the elongated body. The system also includes a control unit in communication with the manually-controlled steerable catheter, the control unit comprising a processor and a memory storing instructions that configure the processor to: receive the image space control commands; determine the roll angle of the distal portion of the elongated body based on the one or more pose determination features; translate the image space control commands into pullwire commands based on the roll angle; and transmit the pullwire commands to the manually-controlled steerable catheter, whereby the elongated body is articulated according to the pullwire commands.

The system can include one or more of the following features in any combination: (a) wherein the one or more pose determination features comprise one or more radio-opaque fiducials positioned on the distal portion of the elongated body, wherein the one or more radio-opaque fiducials are configured such that the roll angle of the distal portion of the elongated body can be determined from the two-dimensional appearance of the one or more radio-opaque fiducials in a medical image that includes a view of the distal portion of the elongated body; (b) wherein the processor is configured to analyze the medical image to determine the roll angle; (c) wherein the one or more pose determination features comprise one or more of: an electromagnetic sensor or a Fiber Bragg grating sensor, and wherein the processor is configured to determine the roll angle based on an output of the an electromagnetic sensor or a Fiber Bragg grating sensor; (d) a medical imager configured to capture the medical image; and a display configured to display the medical image to the user; (e) wherein the steerable catheter comprises a plurality of pullwires configured for articulation of the distal portion of the elongated body; (f) wherein the plurality of pullwires comprise four pullwires configured to allow deflection of the distal portion of the elongated body in four orthogonal directions; (g) wherein the image space control commands allow a user to provide: an in-plane input command to adjust a heading of the steerable catheter within a plane of a medical image; and an out-of-plane input command to adjust an incline of the steerable catheter into or out of the plane of the medical image; and/or other features as described herein.

In another aspect, a method for controlling a manually-controllable steerable catheter, the method includes: receiving, from a user via one or more user inputs on a handle of the steerable catheter, one or more image space control user inputs for controlling the steerable catheter, wherein the image space control user inputs are provided with respect to an imaging plane of an image displayed to a user; transmitting, from the steerable catheter, the image space control user inputs to a processor configured to translate the image space control user inputs to pullwire commands configured to cause articulation of the steerable catheter according to the image space control user inputs, wherein the translation is based on a roll angle of a distal portion of the steerable catheter; receiving, at the steerable catheter, the pullwire commands from the processor; and actuating, at the steerable catheter, one or more motors of the steerable catheter according to the pullwire commands, whereby actuation of the motors causes one or more pullwires of the steerable catheter to articulate the distal portion of the steerable catheter to achieve motion that corresponds with the image space control user inputs.

The method can include one or more of the following features in any combination: (a) wherein the steerable catheter comprises one or more pose determination features configured to allow determination of a roll angle of the distal portion of the steerable catheter; (b) wherein the pose determination features comprise one or more radio-opaque fiducials positioned on the distal portion of the steerable catheter, wherein the one or more radio-opaque fiducials are configured such that the roll angle of the distal portion of the elongated body can be determined from the two-dimensional appearance of the one or more radio-opaque fiducials in a medical image that includes a view of the distal portion of the steerable catheter; (c) wherein the medical image comprise an x-ray image; (d) wherein the one or more pose determination features comprise one or more of: an electromagnetic sensor or a Fiber Bragg grating sensor; (e) wherein the one or more image space control user inputs user inputs are received from a button or a joystick positioned on the handle; (f) wherein the steerable catheter comprises a plurality of pullwires configured for articulation of the distal portion of the elongated body; (g) wherein the plurality of pullwires comprise four pullwires configured to allow deflection of the distal portion of the elongated body in four orthogonal directions; (h) wherein the image space control user inputs comprise: an in-plane input command to adjust a heading of the steerable catheter within a plane of a medical image; and an out-of-plane input command to adjust an incline of the steerable catheter into or out of the plane of the medical image; and/or other features as described herein.

In another aspect, a method for controlling a manually-controllable steerable catheter, the method includes: receiving, from a steerable catheter, one or more image space control user inputs for controlling the steerable catheter, wherein the image space control user inputs are provided by a user with respect to an imaging plane of an image displayed to a user; determining a roll angle of a distal portion of the steerable catheter; based on the image space control user inputs and the roll angle, translating the image space control user inputs to pullwire commands configured to cause articulation of the steerable catheter according to the image space control user inputs; and transmitting the pullwire commands to the steerable catheter, whereby one or motors of the steerable catheter are actuate to cause one or more pullwires of the steerable catheter to articulate the distal portion of the catheter to achieve motion that corresponds with the image space control user inputs.

The method can include one or more of the following features in any combination: (a) wherein the steerable catheter comprises one or more pose determination features configured to allow determination of a roll angle of the distal portion of the steerable catheter; (b) wherein the pose determination features comprise one or more radio-opaque fiducials positioned on the distal portion of the steerable catheter, wherein the one or more radio-opaque fiducials are configured such that the roll angle of the distal portion of the elongated body can be determined from the two-dimensional appearance of the one or more radio-opaque fiducials in a medical image that includes a view of the distal portion of the steerable catheter; (c) wherein the medical image comprises an x-ray image; (d) wherein the one or more pose determination features comprise one or more of: an electromagnetic sensor or a Fiber Bragg grating sensor; (e) wherein the one or more image space control user inputs user inputs are received from a button or a joystick positioned on the handle; (f) wherein the steerable catheter comprises a plurality of pullwires configured for articulation of the distal portion of the elongated body; (g) wherein the plurality of pullwires comprise four pullwires configured to allow deflection of the distal portion of the elongated body in four orthogonal directions; (h) wherein the image space control user inputs comprise: an in-plane input command to adjust a heading of the steerable catheter within a plane of a medical image; and an out-of-plane input command to adjust an incline of the steerable catheter into or out of the plane of the medical image; and/or other features as described herein.

For purposes of this summary, certain aspects, advantages, and novel features are described herein. It is to be understood that not necessarily all such advantages may be achieved in accordance with any particular embodiment. Thus, for example, those skilled in the art will recognize the disclosures herein may be embodied or carried out in a manner that achieves one or more advantages taught herein without necessarily achieving other advantages as may be taught or suggested herein.

All of the embodiments described herein are intended to be within the scope of the present disclosure. These and other embodiments will be readily apparent to those skilled in the art from the following detailed description, having reference to the attached figures. The invention is not intended to be limited to any particular disclosed embodiment or embodiments.

BRIEF DESCRIPTION OF THE DRAWINGS

These and other features, aspects and advantages of the present application are described with reference to drawings of certain embodiments, which are intended to illustrate, but not to limit, the present disclosure. It is to be understood that the attached drawings are for the purpose of illustrating concepts disclosed in the present application and may not be to scale.

DETAILED DESCRIPTION

Figure 1:
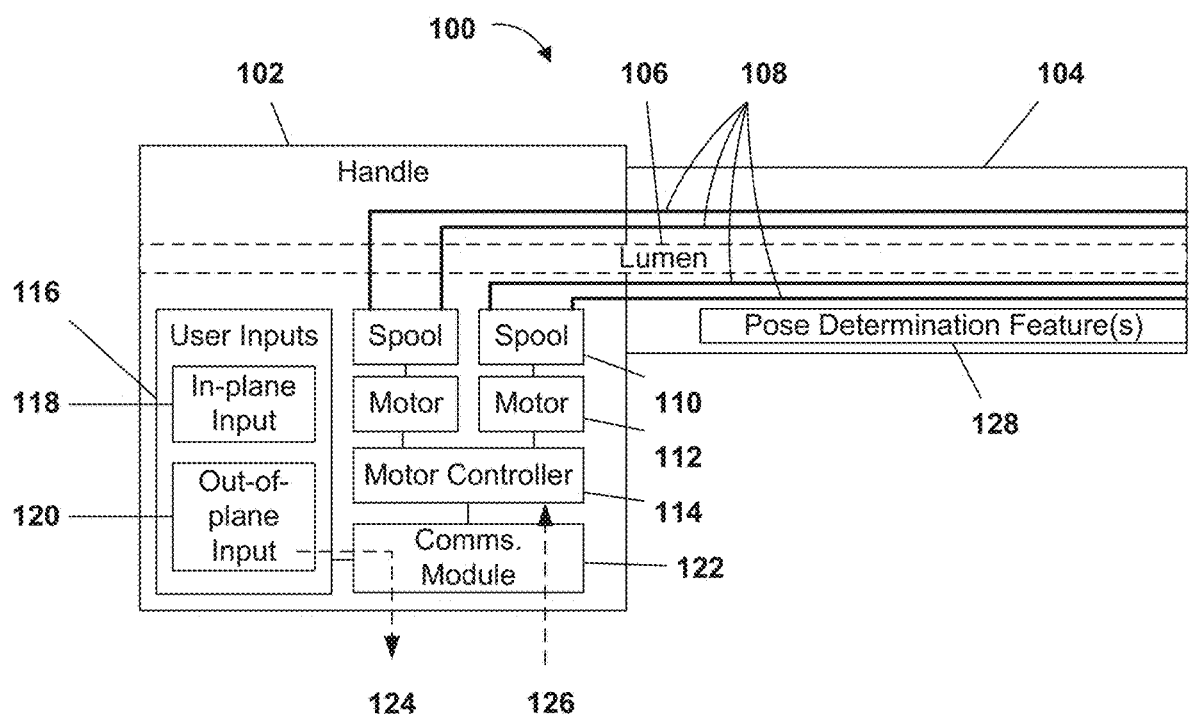
FIG. 1 is a block diagram schematically illustrating an embodiment of a steerable catheter configured for image space control.

This application describes manually-controllable (e.g., handheld or hand operated) intraluminal tools or medical instruments, such as catheters. The catheters are configured such that control inputs are provided in "image space," that is, relative to a plane of a medical image that the operator is viewing. This can facilitate what is referred to herein as "image space control." With image space control, for example, a user may provide control inputs to adjust a heading of the catheter within a plane of the medical and/or or to adjust an incline of the catheter into or out of the plane of the medical image.

This type of catheter and control methodology differs greatly from conventional manually controllable catheters. For example, steerable catheters exist, but doctors rarely use them outside of bronchoscopy, endoscopy, and structural heart intervention. For the majority of endovascular procedures doctors continue to use passive catheters in combination with guidewires to navigate to a target destination. Doctors persist with these methods for several reasons. For example, steerable catheters are very difficult to deflect in a desired direction with respect to how they appear in an x-ray image. This is because catheters roll around passively as they are moved through the vasculature, and the x-ray source (e.g., a C-arm) moves around the patient during the procedure. This means that even though actuating knob 'A' may steer the catheter in a left direction outside of the body, actuating knob 'A' when the catheter is within the vasculature, will not necessarily show the catheter moving left under on the x-ray image. To achieve a desired pose based on the image, doctors would typically need to actuate a combination of pullwires simultaneously, which is very unintuitive and difficult.

For this reason, the majority of endovascular steerable catheters are uni- or bi-directional. That is, the majority of endovascular steerable catheters can only be actuated in one or two directions. To navigate such catheters through the body, the doctor must perform a combination of rolling the catheter about its longitudinal axis and actuating the catheter to achieve a desired pose. Still, this is not always possible in complex anatomy due to variable torque response. Further, a reliance on roll to achieve a desired catheter pose requires steerable catheters to have excellent torque response which invariably makes them large and stiff.

To address one or more of these shortcomings of previously known manually steerable catheters, a new type of steerable catheter is described herein. The steerable catheter described herein can provide safe, intuitive steerability with respect to the x-ray images that the doctor is viewing during a procedure. This provides several benefits including ease of navigability which leads to faster procedure times resulting in reduced x-ray exposure for patients, improved time to treatment for time critical cases, and reduced anesthetic time. This also can reduce vessel trauma due to the improved precision of navigation.

FIG. 1 is a block diagram schematically illustrating an embodiment of a steerable catheter 100 configured for image space control. As shown, the catheter 100 includes a handle 102 and an elongated body 104. The elongated body 104 can be configured as a long and thin flexible body (not shown to scale in the figure) that is configured for insertion into the body, for example, into a lumen of the body. The elongated body 104 can include a lumen 106 formed therethrough that can allow one or more tools to be telescoped therethrough. In some embodiments, the lumen 106 can also be used for irrigation, aspiration, and/or contrast injection. The handle 102 can be configured to be held by an operator, for example, a doctor, who controls the catheter 100 during the procedure. In some embodiments, the handle 102 is configured to be operated by only a single hand.

As shown in FIG. 1, one or more pullwires 108 extend from spools 110 in the handle 102 to the distal end of the elongated body 104. By actuating (e.g., rotating) the spools 110, the pullwires 108 can impart forces on the distal end of the body 104 that cause it to deflect or articulate. In some embodiments, the catheter 100 includes 4 pullwires 108 oriented at 90 degrees with respect to each other to cause articulation in four different directions. Other pullwire configurations can be used as well, such as eight pullwires 108. Within the handle 102, motors 112 can be coupled to the spools 110, which, when driven by a motor controller 114, cause the spools 110 to rotate thereby causing the articulation of the elongated body 104.

With further reference to FIG. 1, the handle 102 can also include one or more user inputs 116 configured to allow the user to provide inputs 118, 120 for articulating the elongated body 104. As described above, the catheter 100 can be configured for image space control, such that commands are provided with respect to the plane of a medical image 804 (see FIG. 8) that the doctor is using to view the distal end of the catheter 100 during a procedure. Accordingly, as illustrated in FIG. 1, the user inputs can include an in-plane input 118, and an out-of-plane input 120. The in-plane input 118 can indicate a desire to articulate the elongated body 104 within the plane of the medical image 804. The out-of-plane input 120 can indicate a desire to articulate the elongated body 104 out of or into the plane of the medical image 804. Thus, the inputs 118, 120 provided via the user inputs 116 are considered image space control inputs 124 because they are provided with respect to the image plane of a medical image 804. Although not illustrated in FIG. 1, other types of user inputs 116 can also be provided on the handle, such as for example, a user input 116 that allows for contrast injection. The user inputs 116 can comprise buttons, joysticks, knobs, and the like.

Figure 5:
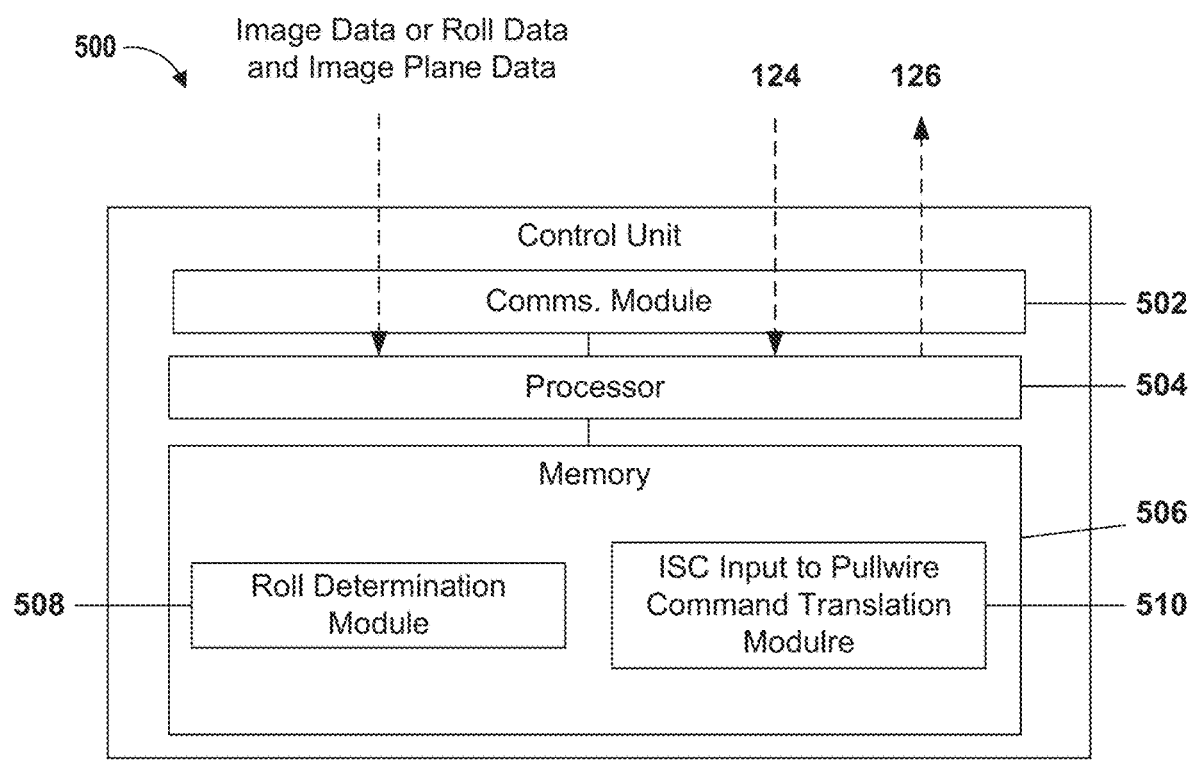
FIG. 5 is a block diagram schematically illustrating an embodiment of a control unit configured for use with the steerable catheter of FIG. 1.

Most notably, as illustrated in FIG. 1, the user inputs 116 are not directly coupled (e.g., mechanically linked) to the motors 112 or spools 110 of the handle 102 as would be common in typical steerable catheters. Rather, the user inputs 116 are provided to a communications module 122 which sends the image space control inputs 124 to a control unit (such as illustrated in FIG. 5), which determines appropriate pullwire commands 126 to cause the desired motion. The pullwire commands 126 are then received back at the communications module 122 and transmitted to the motor controller 114 which causes the motor controller 114 to operate the motors 112 to actuate the pullwires 108. The communications module can be a wireless module (e.g., WiFi, Bluetooth, etc.) or a wired communications module (e.g., ethernet, etc.).

As shown in FIG. 1, the steerable catheter 100 can also include one or more pose determination features 128 positioned on the elongated body 104, for example, at or proximal a distal end or tip of the elongated body 104 that can be configured to facilitate determination of the pose of the steerable catheter 100 or to facilitate determination of the pose of the distal portion of the steerable catheter 100.

In some instances, the term "pose" is used herein to refer to the position and orientation of the distal portion or tip of the steerable catheter 100. In some embodiments, determination of pose can be made based on a two-dimensional medical image 804 (See FIG. 8), such as a single plane x-ray image, and one or more radio-opaque markers included on the steerable catheter 100. Computer vision models can be employed to detect the radio-opaque markers in the two-dimensional medical image 804 and to determine the pose of the catheter 100 therefrom. In some instances, the pose can be defined by five degrees of freedom for the catheter 100. The five degrees of freedom can include two positional degrees of freedom (e.g., x and y position) and three degrees of freedom relating to orientation (e.g., heading, incline, and roll). In other embodiments, the pose can comprise greater (e.g., six) or fewer (e.g., four or fewer) degrees of freedom. The pose of an instrument can be defined in many different ways. While this application primarily describes examples of pose in terms of x, y, and z for position, and heading, incline, and roll for orientation, other methods for describing or defining the pose (e.g., alternative coordinate systems, alternative naming conventions, etc.) are possible, and the principles of this application extend to all methods for defining pose. Further, in some embodiments, the methods and systems of this application may be used to determine one, more than one, or all elements of pose.

Figure 2A:
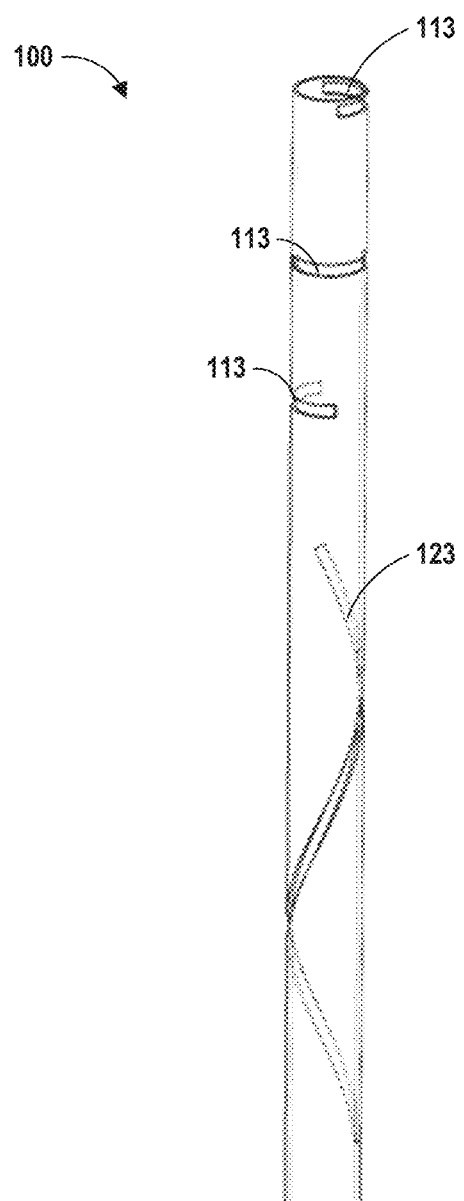
FIG. 2A is a perspective view of distal end of an embodiment of a steerable catheter which includes embodiments of fiducials thereon, wherein the fiducials are configured to facilitate determination of the pose of the steerable catheter to facilitate image space control.
Figure 2B:
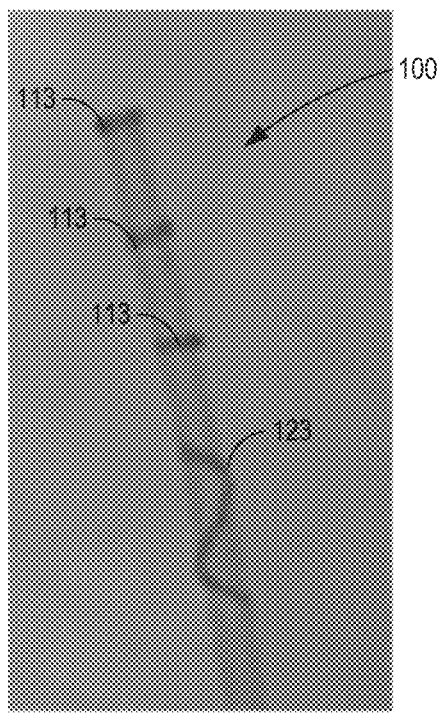
FIGS. 2B-2E are example fluoroscopic images of the steerable catheter and fiducials of FIG. 16A shown with different poses.
Figure 2C:
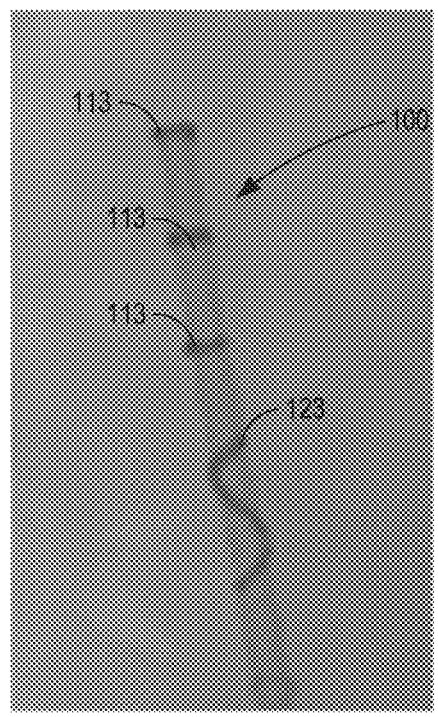
Figure 2D:
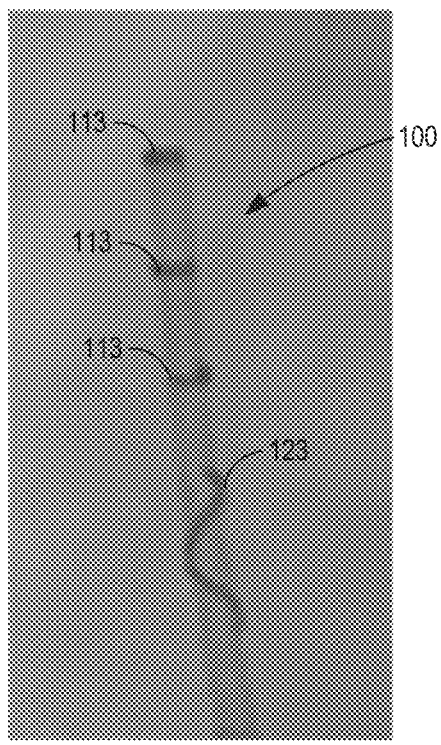
Figure 2E:
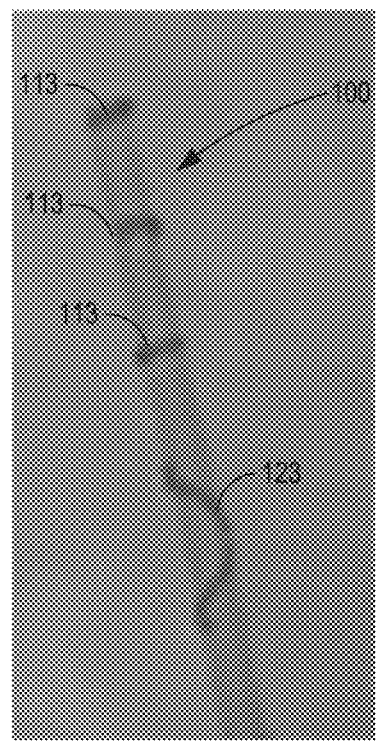

FIG. 2A provides an example of a distal portion of a steerable catheter 100 that includes radio-opaque markers 113, 123 positioned thereon to facilitate determination of pose. Although FIG. 2A illustrates one example arrangement of markers 113, 123 on the steerable catheter 100, other configurations are also possible. Numerous configurations of radio-opaque rotation fiducials 113, 123 can be utilized to determine the degree of tool rotation, provided the configurations result in a unique x-ray appearance of the tool 100 at differing degrees of rotation and/or incline. While multiple configurations will be disclosed with reference to certain embodiments, it will be understood that various changes may be made, and equivalents may be substituted for elements thereof without departing from the scope of the disclosure. In some embodiments, a computer vision algorithm can be used to detect and analyze the positions of the markers 113, 123 to determine the rotation or roll of the catheter 100 about its longitudinal axis. As described above, the roll angle of the catheter 100 determines how an actuation of a given pull wire 108 will move the catheter 100. Thus, an accurate understanding of the roll angle of the catheter 100 can be important for successful navigation of the catheter 100 through the vasculature.

In the illustrated embodiment of FIG. 2A, a radio-opaque one and one quarter helix fiducial 123 is coupled to catheter 100, where the helix is made slightly longer than one complete revolution, such that the helix fiducial 123 is approximately 1.25 times the articulation length. The degree of roll of catheter 100 can be determined because the helix fiducial 123 takes on a different appearance depending on the degree of roll. In FIG. 2A, the helix fiducial 123 can comprise other lengths greater than or less than one and one quarters. For example, as shown in FIGS. 2B-2E, at different degrees of roll, the helix fiducial 123 takes on a distinct appearance. In some embodiments, the articulation length is approximately two centimeters. The embodiments illustrated in FIGS. 2A-2E also include examples of the non-circumferential markers 113.

Figure 3A:
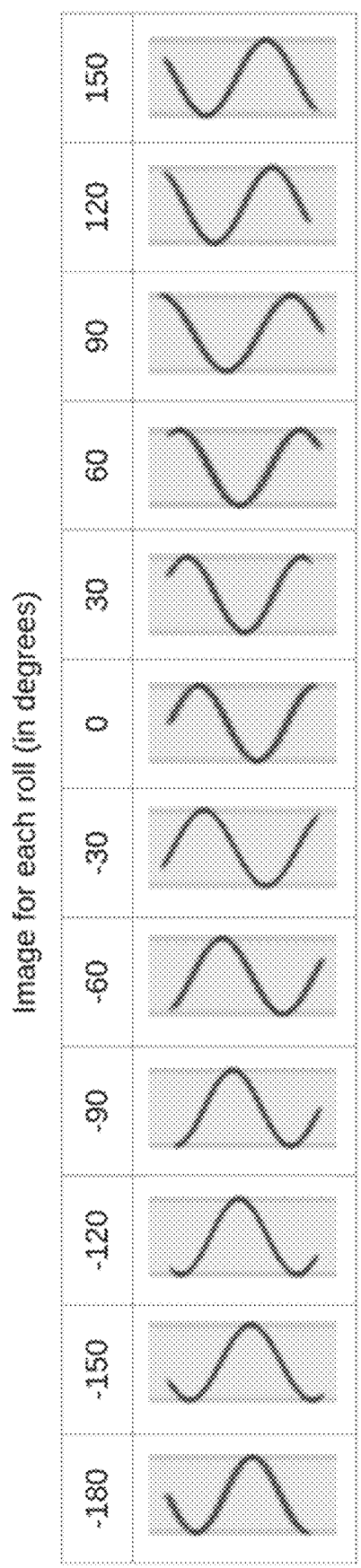
FIG. 3A is a table showing the appearance of an embodiment of a fiducial at different roll angles.

FIG. 3A illustrates the two-dimensional appearance (e.g., as within the plane of medial image) of the helix fiducial 123 of FIG. 2A and different roll positions in 30-degree increments. As shown, each roll position provides a unique appearance which can be used to determine roll, for example, by a computer vision, neural network, or machine learning system. While FIG. 3A illustrates how the helix fiducial 123 provides different two-dimensional appearances for different roll positions at 30-degree increments, the illustrated increments are not intended to be limiting.

In some embodiments, the radio-opaque markers 113, 123 provide unique or visually distinguishable two-dimensional appearances at all different roll positions. In some embodiments, the radio-opaque markers 113, 123 provide unique or visually distinguishable two-dimensional appearances at different roll positions within increments of about, at least, or at most 1 degree, 2 degrees, 3 degrees, 4 degrees, 5 degrees, 7.5 degrees, 10 degrees, 12.5 degrees, 15 degrees, 17.5 degrees, 20 degrees, 25 degrees, 30 degrees, or 40 degrees. The above listed increments can be considered minimum resolutions for the system or the minimum change in roll that is detectable by the system.

In some embodiments, the roll angle determined based on the markers 113, 123 of any of these embodiments can be used to determine pullwire commands 126 to articulate the steerable catheter 100. In one embodiment, an algorithm can be configured to rotate the catheter 100 until the radio-opaque identifiers 113, 123 align with the imaging plane. In another embodiment, the algorithm can measure the rotation of the tool using the radio-opaque identifiers 113, 123 and update which pull wires 108 it uses to execute a maneuver.

The embodiments of the markers 113, 123 illustrated in FIG. 2A are also configured to provide determination of the sign and magnitude of incline of catheter 100. In the illustrated example, the catheter 100 can include one or more non-circumferential rings 113. In the illustrated embodiment, the non-circumferential rings are semi-circular, extending part way around the catheter 100. In some embodiments, the non-circumferential rings 113 can be radio-opaque such that it can easily be identifiable within a medical image 804. The appearance of the non-circumferential rings 113 can be analyzed to determine the sign and magnitude of the incline of the catheter 100. The sign and magnitude of the incline of catheter 100 can be determined by the unique appearance of the non-circumferential rings 113 in the two-dimensional image at varying degrees of incline, both positive and negative. In some embodiments, non-circumferential rings 113 are arranged in an asymmetrical design. That is, in some embodiments, the non-circumferential rings 113 are each positioned at a different rotational position around the catheter 100. In the illustrated embodiments, the non-circumferential rings are positioned at 90-degree offsets. In some embodiments, non-circumferential rings 113 are multiple ellipses offset from each other.

Figure 3B:
FIG. 3B is a table showing the appearance of an embodiment of a fiducials at different roll angles and inclined positions.

FIG. 3B illustrates how an example arrangement of non-circumferential rings 113 positioned on a distal end of a catheter 100 may provide a unique appearance at different inclination and roll angles. Images are provided at positive, neutral (i.e., zero), and negative inclinations, as well as at different roll positions provided in 30-degree increments. As shown, each of the 36 different illustrated positions provides a unique appearance. By detected, for example, using computer vision, this appearance within a medical image 804, the incline (including its sign) and the roll of the catheter can be determined. While FIG. 3B illustrates how the radio-opaque non-circumferential rings 113 can provide different two-dimensional appearances for different roll positions at 30-degree increments and for different positive, neutral (zero), and negative inclines, the illustrated increments are not intended to be limiting.

In some embodiments, the radio-opaque markers 113, 123 provide unique or visually distinguishable two-dimensional appearances at all different roll or incline positions. In some embodiments, the radio-opaque markers 113, 123 provide unique or visually distinguishable two-dimensional appearances at different roll or incline positions within increments of about, at least, or at most 1 degree, 2 degrees, 3 degrees, 4 degrees, 5 degrees, 7.5 degrees, 10 degrees, 12.5 degrees, 15 degrees, 17.5 degrees, 20 degrees, 25 degrees, 30 degrees, or 40 degrees. That is, in some embodiments, the radio-opaque markers 113, 123 are configured with a three-dimensional shape that, when viewed within the two-dimensional plane of a two-dimensional medical imaging device, provides a unique or visually distinguishable appearance that can be distinguished at the different incremental roll or incline angles listed above. The above listed increments can be considered minimum resolutions for the system or the minimum change in roll or incline that is detectable by the system.

Although FIGS. 2A-3B have described examples where the pose determination features 128 included on the steerable catheter 100 comprise radio-opaque markers 113, 123, the appearance of which can be analyzed to determine pose, other mechanisms can also be used. For example, pose determination features 128 can also include electromagnetic (EM) sensor(s) or Fiber Bragg grating sensor(s) that provide outputs from which pose can be determined.

Figure 4:
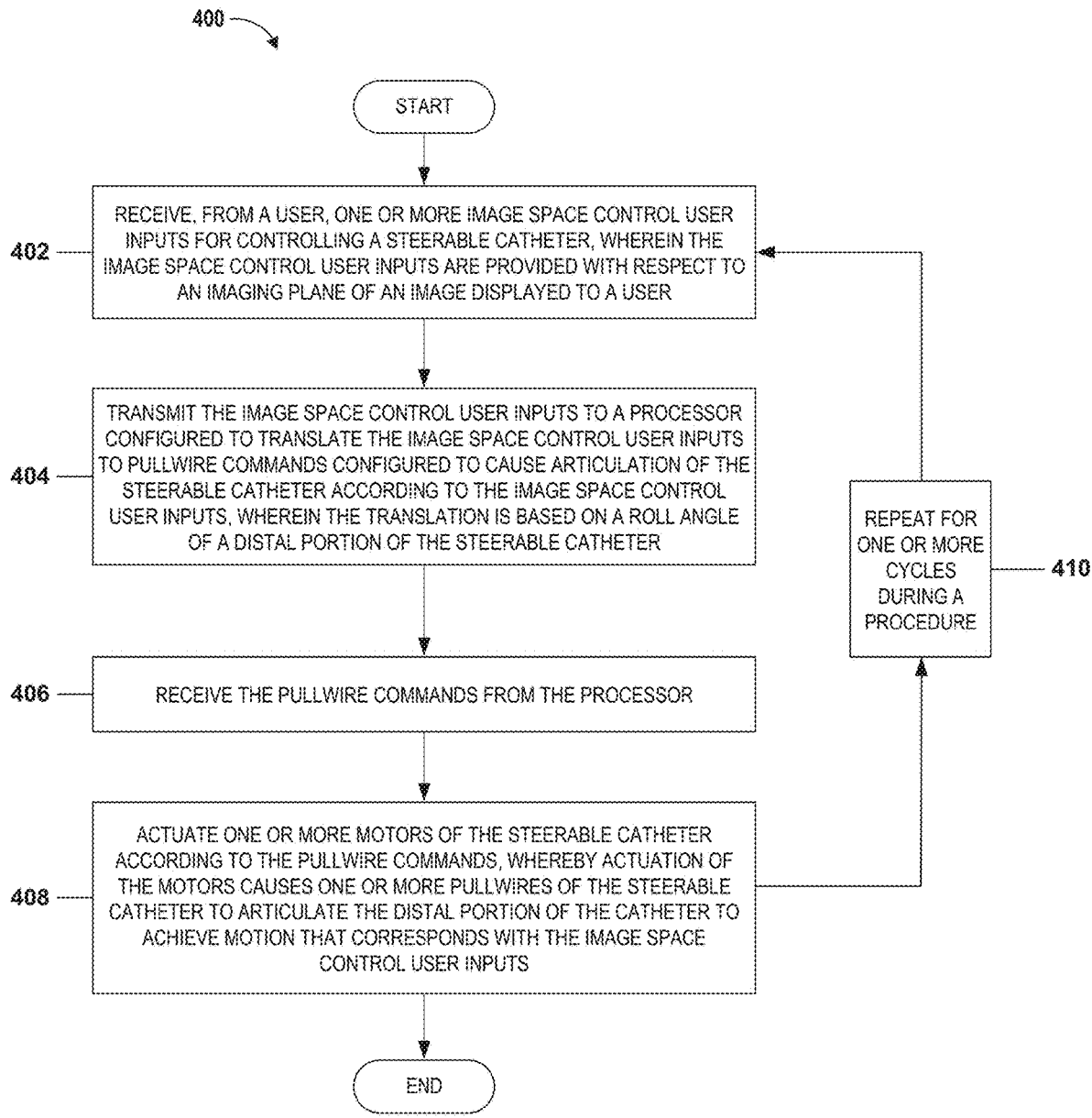
FIG. 4 illustrates an example method associated with the steerable catheter of FIG. 1.

FIG. 4 illustrates an example method 400 associated with the steerable catheter 100 of FIG. 1. As illustrated, in a first step 402, the method includes receiving, from a user (e.g., the doctor holding the catheter), one or more image space control user inputs 124 for controlling a steerable catheter 100, wherein the image space control user inputs 124 are provided with respect to an imaging plane of an image displayed to a user. Notably, the user provides these inputs with respect to the imaging plane of the medical image 804, and without regard for the current roll orientation of the catheter 100, as would typically be required for operating a steerable catheter.

As a next step 404, the method 400 includes transmitting the image space control user inputs 124 to a processor 504 (see FIG. 5) configured to translate the image space control user inputs 124 to pullwire commands 126 configured to cause articulation of the steerable catheter 100 according to the image space control user inputs 124, wherein the translation is based on a roll angle of a distal portion of the steerable catheter 100. Here, the processor 504, using a roll estimate for the catheter 100, determines how to actuate the pullwires 108 to achieve the user's desired motion. The roll estimate can be determined in various ways, such as based on the appearance of fiducials 113, 123 on the catheter 100, based on the output of an EM sensor or Fiber Bragg grating sensor, or as input by the user 116. Once determined, the pullwire commands 126 are sent back to the catheter 100, which as a next step 406, receives the pullwire commands 126 from the processor 504.

In a next step 408, the method 400 includes actuating the one or more motors 112 of the steerable catheter 100 according to the pullwire commands 126, whereby actuation of the motors 112 causes one or more pullwires 108 of the steerable catheter 100 to articulate the distal portion of the catheter 100 to achieve motion that corresponds with the image space control user inputs 124. The method 400 can be repeated 410 for one or more cycles during a procedure.

FIG. 5 is a block diagram schematically illustrating an embodiment of a control unit 500 configured for use with the steerable catheter 100 of FIG. 1. In the illustrated embodiment, the control unit 500 includes a communications module 502, a processor 504, and a memory 506. The memory 506 can include one or more modules that configure the processor 500 to perform certain tasks. In the illustrated embodiment, the memory 506 includes a roll determination module 508 and an ISC input to pullwire command translation module 510.

The roll determination module 508 can be configured to determine a current roll estimate for the distal end of the catheter 100. In some embodiments, this is based on a computer vision or machine learning analysis of the medical image 804. For example, the catheter 100 can include a fiducial 113, 123 on the distal end thereof, the appearance of which in the medical image 804 can be analyzed to determine current roll of the instrument 100. Alternatively, roll can be determined based on the output of a sensor (such as an EM sensor or FBG sensor) in combination with a position of the C-arm. In a further embodiment, roll can be provided by the user as in input 116.

The ISC input to pullwire commend translation module 510 can be configured to receive the roll estimate from the roll determination module 508 as well as the ISC user inputs 124 provided by the user and translate them into appropriate pullwire commands 126 to cause the desired motion.

Figure 6:
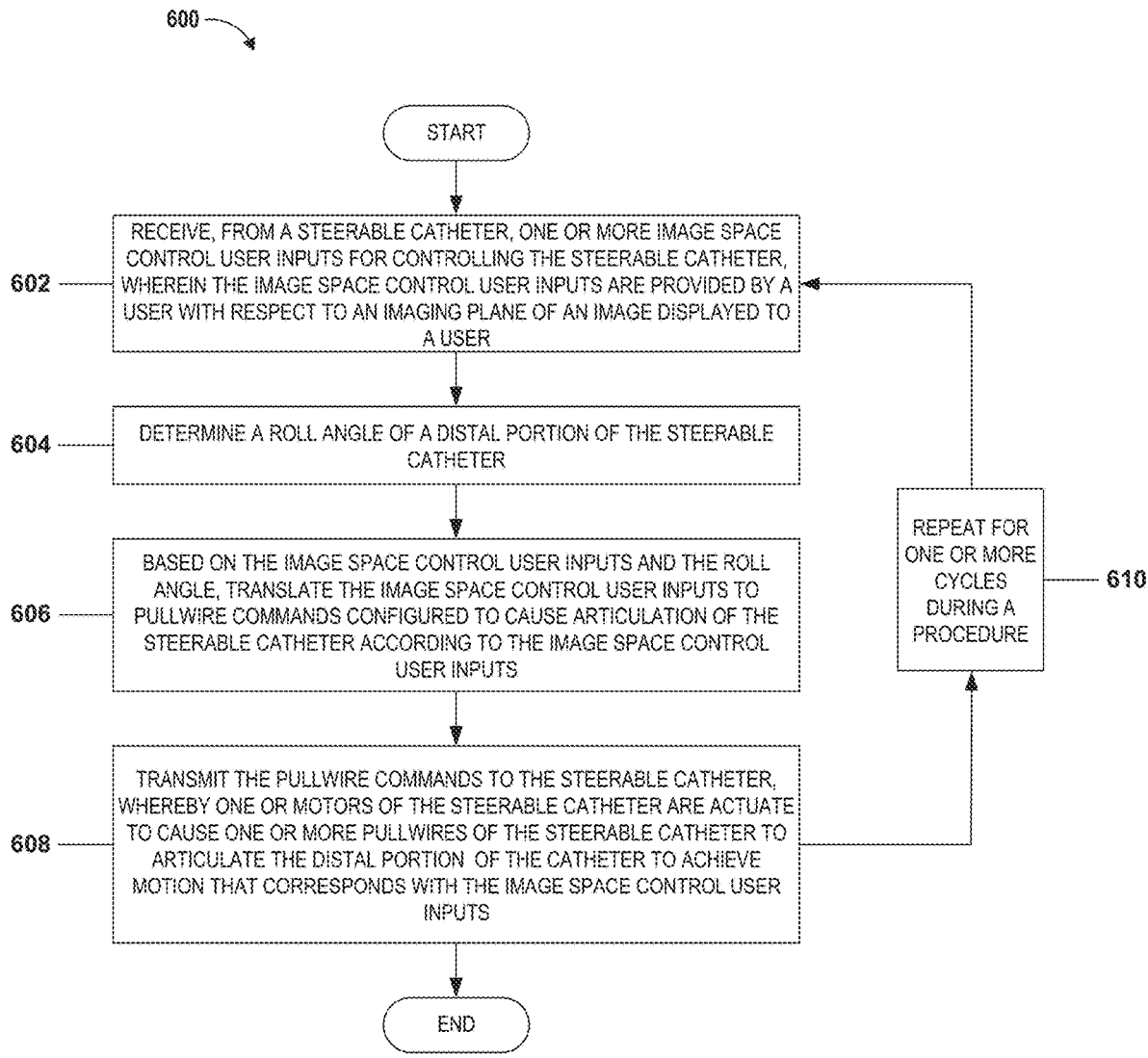
FIG. 6 illustrates an example method associated with the control unit of FIG. 5.

FIG. 6 illustrates an example method 600 associated with the control unit 500 of FIG. 5. In a first step 602, the method 600 can include receiving, from a steerable catheter 100, one or more image space control user inputs 124 for controlling the steerable catheter 100, wherein the image space control user inputs 124 are provided by a user with respect to an imaging plane of an image displayed to a user.

As a next step 604, the method 600 can include determining a roll angle of a distal portion of the steerable catheter 100. In some embodiments, this is based on a computer vision or machine learning analysis of the medical image 804. For example, the catheter 100 can include a fiducial 113, 123 on the distal end thereof, the appearance of which in the medical image 804 can be analyzed to determine current roll. Alternatively, roll can be determined based on the output of a sensor (such as an EM sensor or FBG sensor) in combination with a non-position of the C-arm. In a further embodiment, roll can be provided by the user as in input 116.

In a next step 606, the method 600 can include, based on the image space control user inputs 124 and the roll angle, translating the image space control user inputs 124 to pullwire commands 126 configured to cause articulation of the steerable catheter 100 according to the image space control user inputs 124.

In a final step 608, the method 600 can include transmitting the pullwire commands 126 to the steerable catheter 100, whereby one or motors 112 of the steerable catheter 100 are actuated to cause one or more pullwires 108 of the steerable catheter 100 to articulate the distal portion of the catheter 100 to achieve motion that corresponds with the image space control user inputs 124. The method 600 can be repeated 610 for one or more cycles during a procedure.

Figure 7:
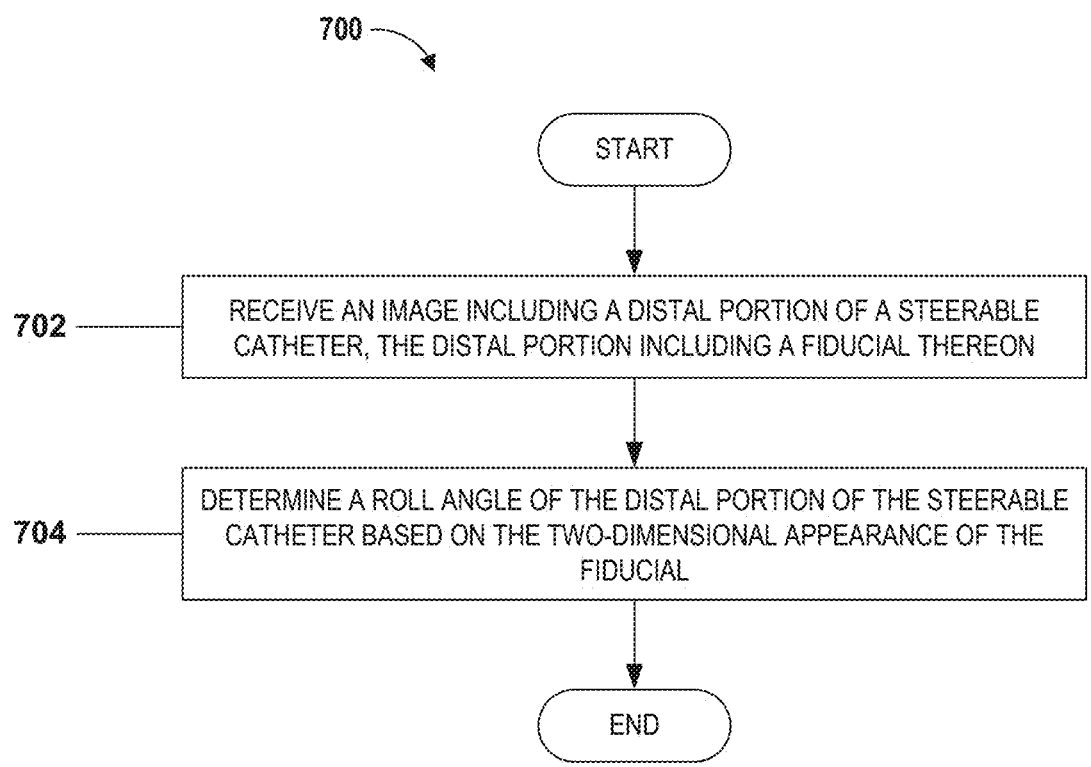
FIG. 7 illustrates another example method associated with the control unit of FIG. 5.

FIG. 7 illustrates another example method 700 associated with the control unit 500 of FIG. 5. In particular, the method 700 of FIG. 7 provides further detail about how the roll angle of the catheter 100 can be determined in some embodiments where the catheter includes a roll fiducial 113, 123. In a first step 702, the method can include receiving an image including a distal portion of a steerable catheter 100, the distal portion including a fiducial 113, 123 thereon.

As a next step 704, the method 700 can include determining a roll angle of the distal portion of the steerable catheter 100 based on the two-dimensional appearance of the fiducial 113, 123.

Figure 8:
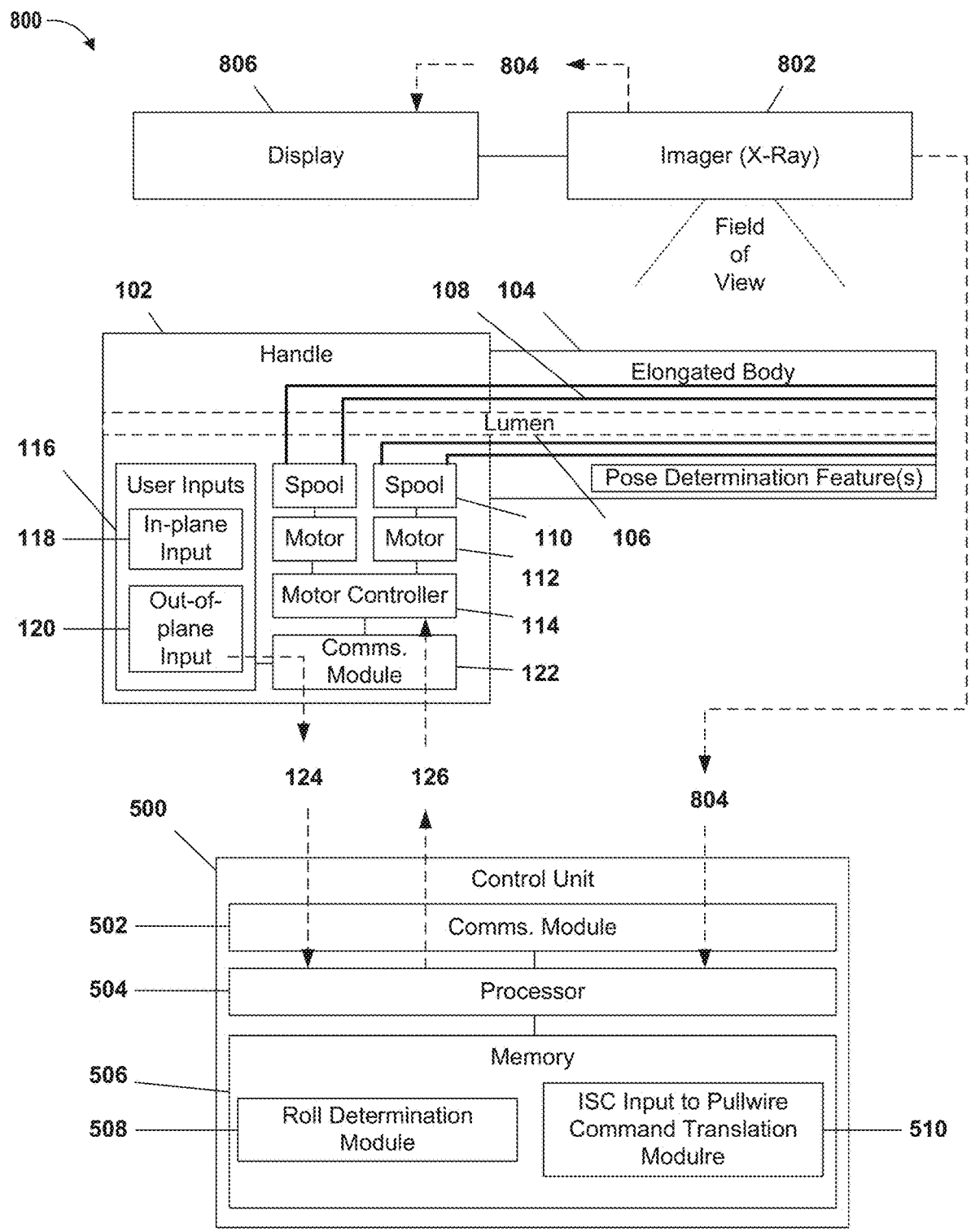
FIG. 8 is a block diagram illustrating an embodiment of a system that includes the steerable catheter of FIG. 1 and the control unit of FIG. 5.

FIG. 8 is a block diagram illustrating an embodiment of a system 800 that includes the steerable catheter 100 of FIG. 1 and the control unit 500 of FIG. 5. As shown, the system 800 further includes an imager 802 for generating a medical image 804, such as an x-ray, and a display 806 for displaying the medical image 804 to the user. As shown in FIG. 8, the imager 802 captures a medical image 804 that includes a view of a distal portion of the elongated body 104 of the catheter 100. The medical image 804 is displayed to the user who views the image 804 on the display 806 and controls the catheter 100 based on the image 804. Using the user inputs 116 on the handle, the user provides ISC control inputs 124. Again, these are inputs 124 that are provided with respect to the plane of the medical image 804. That is, if the user can provide an in-plane input 118 to articulate the catheter 100 within the plane of the image 804, and an out-of-plane input 120 to articulate the catheter 100 into or out of the plane of the image 804. As shown, the ISC inputs 124 are provided to the control unit 500 that determines appropriate pullwire commands 126 to cause the desired motion, and these pullwire commands 126 are provided back to the catheter 100 where they are implemented.

Figure 9:
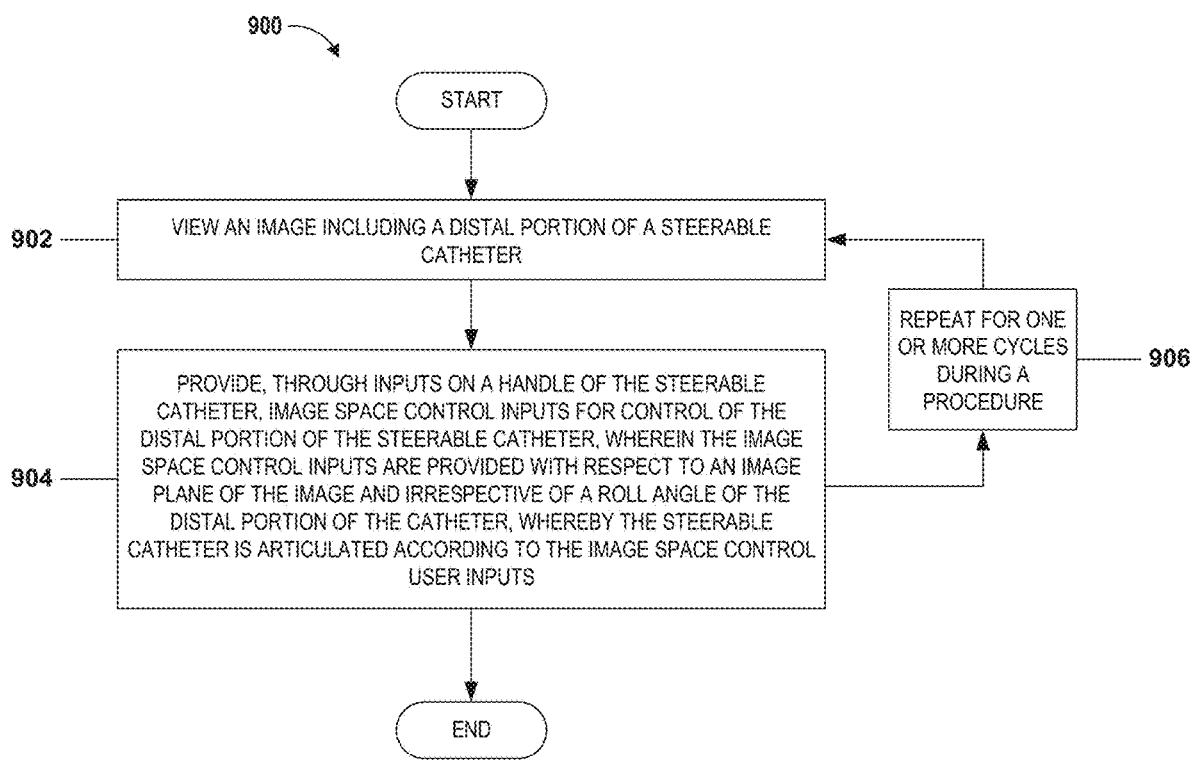
FIG. 9 illustrates an example method of using the steerable catheter of FIG. 1 in the system of FIG. 8.

FIG. 9 illustrates an example method 900 of using the steerable catheter 100 of FIG. 1 in the system 800 of FIG. 8. In a first step 902, the doctor views an image 804 including a distal portion of the catheter 100 on the display 806. As a next step 904, the doctor provides through inputs 116 on a handle 102 of the steerable catheter 100, image space control inputs 124 for control of the distal portion of the steerable catheter 100, wherein the image space control inputs 124 are provided with respect to an image plane of the image 804 and irrespective of a roll angle of the distal portion of the catheter 100, whereby the steerable catheter 100 is articulated according to the image space control user inputs 124. The method 900 can be repeated 906 for one or more cycles during a procedure.

Figure 10:
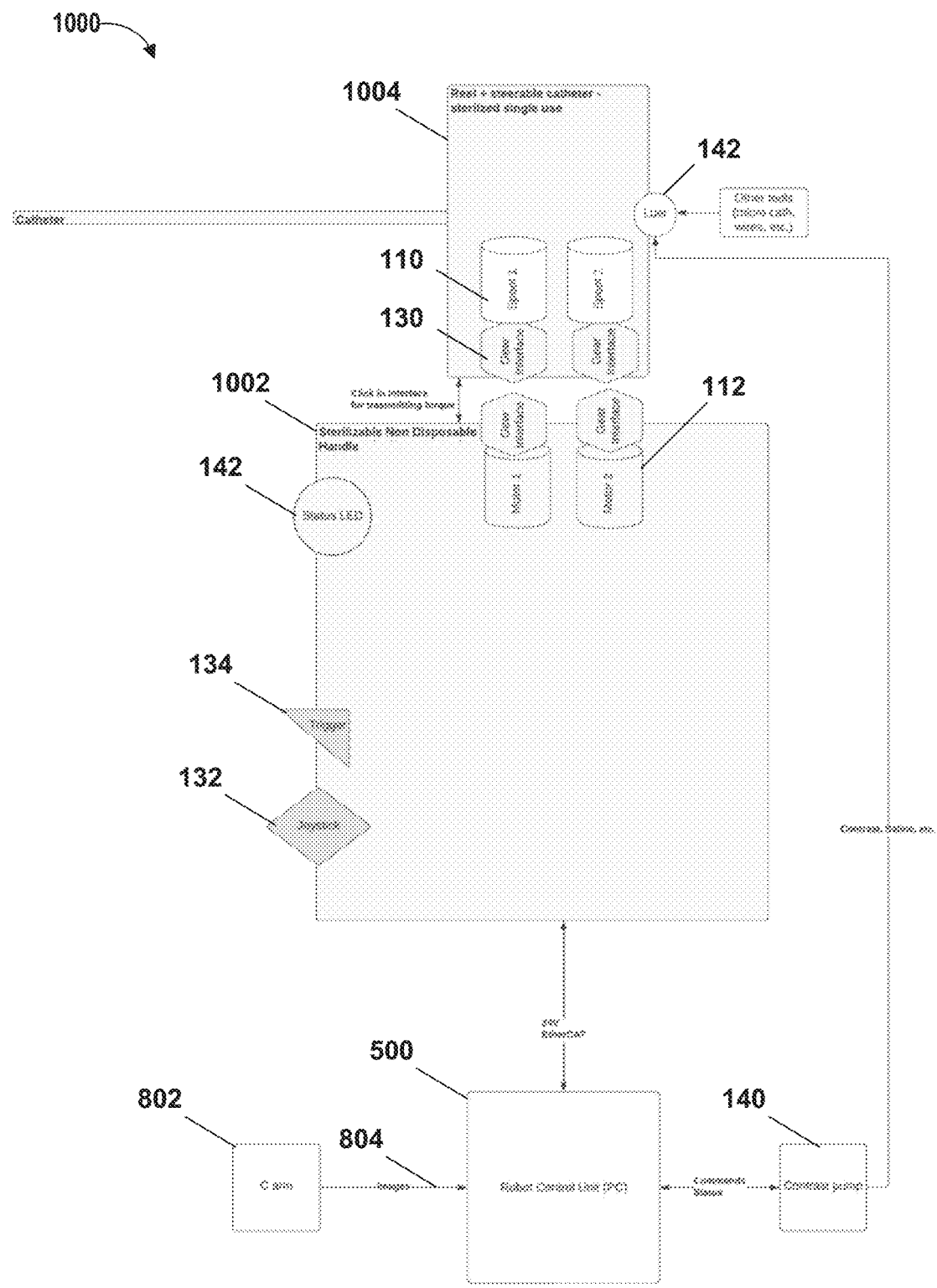
FIG. 10 is a schematic illustration of an embodiment of a steerable catheter system configured for image space control that includes a single use steerable catheter and a multiuse handle.

FIG. 10 is a schematic illustration of an embodiment of a steerable catheter system 1000 configured for image space control that includes a single use steerable catheter 1004 and a multiuse handle 1002. In this embodiment, the catheter system 1000 includes a catheter 1004 and base 1002, which together provide the functionality described above. An advantage of this system is that it separates the catheter 100 of FIG. 1 into two components: a disposable catheter 1004, and a sterilizable handle or base 1002 (referred to as a magic wand in the figure). Here, one can see that the spools 110 are located in the disposable catheter 1004 and that the motors 112 are located in the handle 1002. The spools 110 and motors 112 interface via gear interfaces 130 such that the catheter 1004 can be removably coupled to the handle 1002 in a manner that provides adequate torque response to the catheter 1004. After use of the steerable catheter system 1000, the user can remove and dispose of the single use disposable catheter 1004 and sanitize the handle 1002 for future use. In a subsequent procedure, the user can attach a new disposable catheter 1004 to the previously used and sanitized handle 1002.

FIG. 10 also illustrates that the user inputs 116 can include a joystick 132 (for providing the ISC inputs 124) and a trigger 134 for controlling injection of contrast or saline. These are provided by way of example and other control inputs 116 can be provided. FIG. 10 also illustrates the C-arm 802 (imager), robot control pc 500 (control unit), and a contrast pump 140. As shown in FIG. 10, the disposable catheter 1004 can also include a Luer connector 142 configured to receive and couple other tools to the disposable catheter 1004, for example, micro catheters and wires. Additionally, FIG. 10 shows that the handle 1002 can include a status light-emitting diode ("LED") 144.

Figure 11:
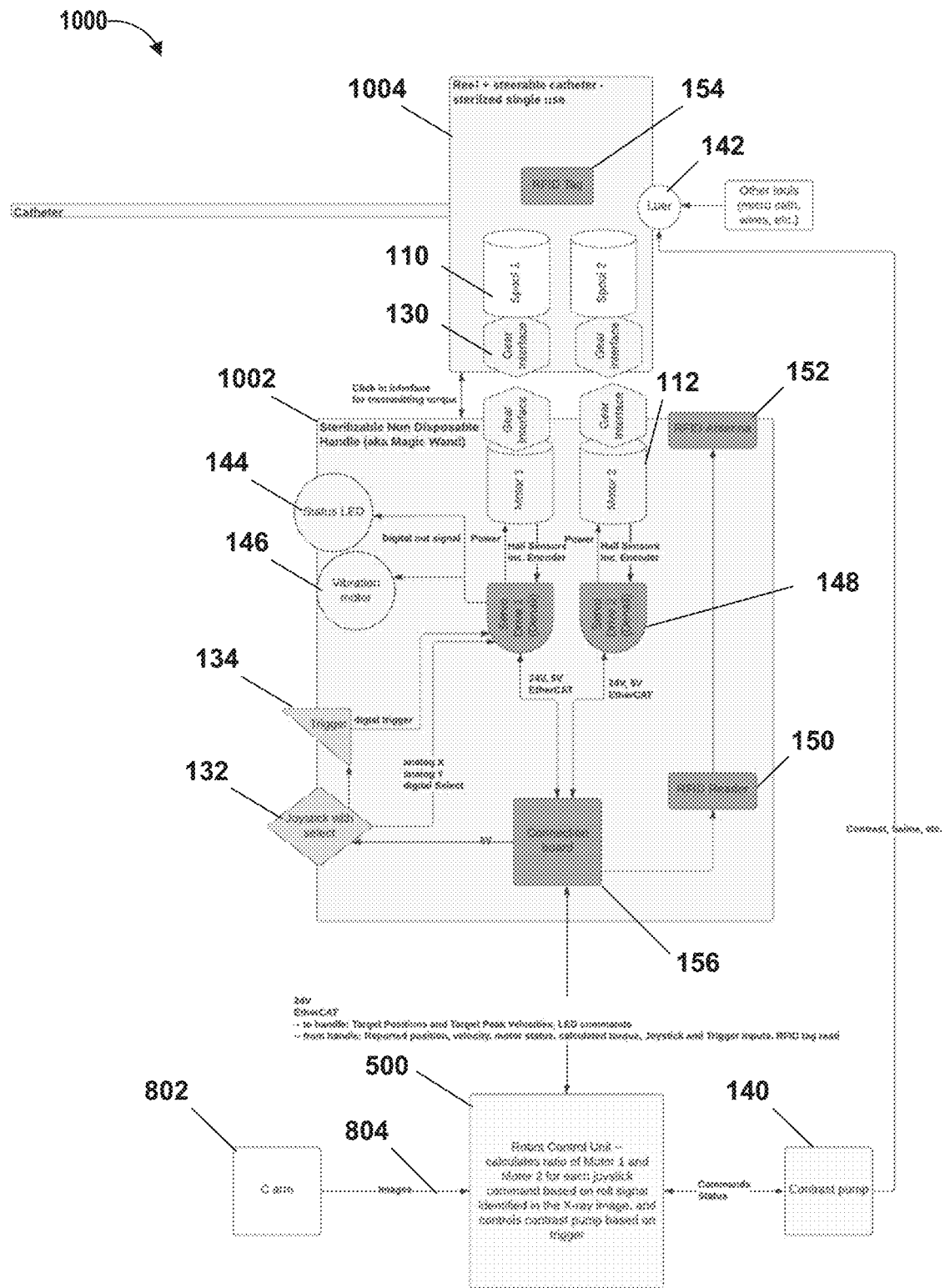
FIG. 11 illustrates example electric connections and additional components of the steerable catheter system of FIG. 10.

FIG. 11 illustrates example electric connections and additional components of the steerable catheter system 1000 of FIG. 10. As shown in the exemplary embodiment, the handle 1002 can include a vibration motor 146, at least one servo drive 148), an radio frequency identification ("RFID") reader 150 and tag 152 and a connection board 156. Although the number of servo drives 146 equals the number of motors 112 in the embodiment shown by FIG. 11, it should be appreciated that this not need be the case in all embodiments. For example, in some embodiments there can be two motors 112 and one servo drive 148.

The connection board 156 of the handle 1002 can be configured as a communication terminal to transmit information between the robot control unit 500 and the various components of the handle 1002. For example, the connection board 156 can send information to the robot control unit 500 regarding the reported position and velocity of the single use disposable catheter 1004, the status of the at least one servo motors 148, calculated torques, image space control inputs 124 entered with the control inputs 116 (in FIG. 11, these are shown as the joystick 132 and trigger 134) and RFID tag 154 readings. The connection board 156 can transmit to the components of the handle 1002 information from the robot control 500 unit regarding target positions and velocities and LED commands to be output by the status LED 144.

As shown in FIG. 11, the single use steerable catheter 1004 includes an RFID tag 154 that can be configured to interact with the RFID reader 150 and RFID antenna 152 of the handle 1002. The RFID tag 154 can, for example, be configured to communicate to the RFID reader 150 and RFID antenna 152 that a tool has been attached to the single use steerable catheter 1004, for example, with the Luer connector 142.

Figure 12:
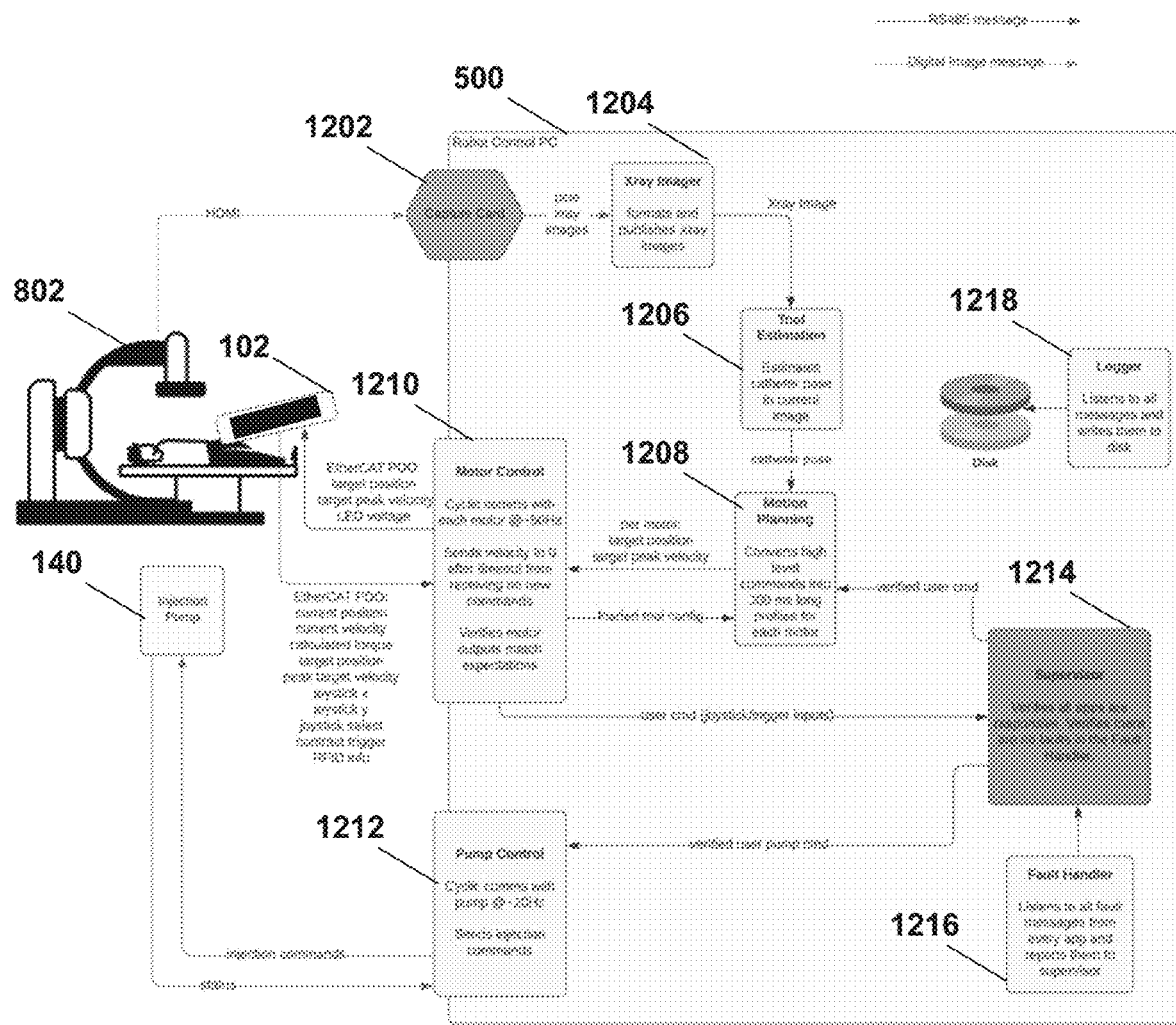
FIG. 12 is a schematic illustration of a control architecture for a steerable catheter configured for image space control.
Figure 13B:
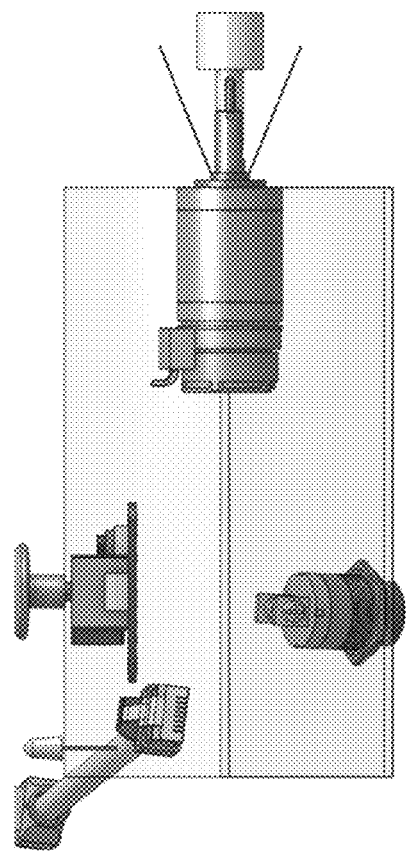
FIGS. 13A-13D illustrate various views of an embodiment of a steerable catheter system configured for image space control.
Figure 13D:
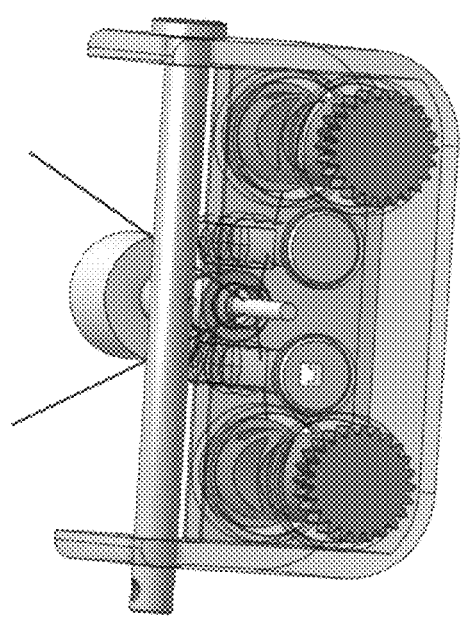
Figure 13C:
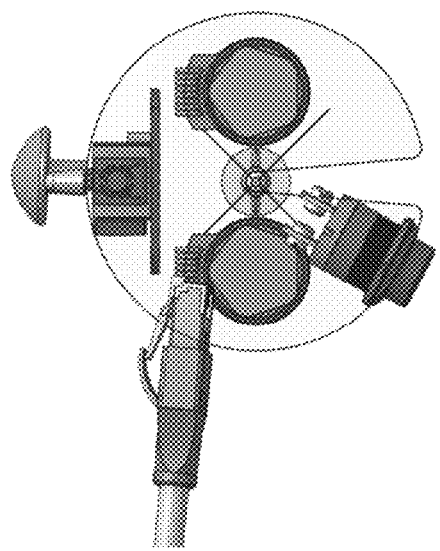
Figure 13A:
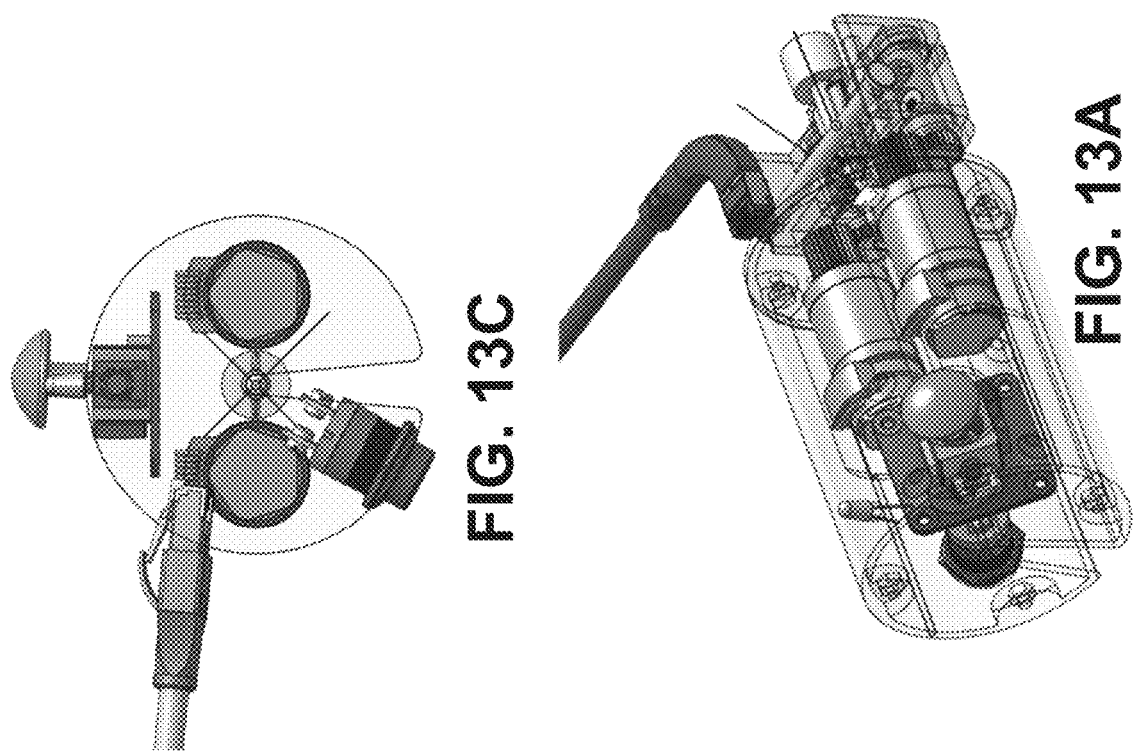

FIG. 12 is a schematic illustration of a control architecture for a steerable catheter configured for image space control. As shown in the exemplary embodiment, the robot control pc 500 (controller unit) can include a capture card 1202, an x-ray imager 1204, a tool estimation module 1206, a motion planning module 1208, a motor controller 1210, a pump controller 1212, a supervisor 1214, a fault handler module 1216 and a logger 1218.

As shown in FIG. 12, the C-arm 802 (imager) can be connected to the capture card 1202 via an HDMI cord to transmit the displayed medical image 804 to the robot controller pc 500. The capture card 1202 can then provide the medical image 804 to the x-ray imager 1204 that can format the medical image 804 for use by the tool estimation module 1206. The tool estimation module 1208 can use the formatted medical image 804 to estimate a pose of the catheter 100 in the current displayed medical image 804. The estimation can be transmitted to the motion planning module 1208. The handle 102 of the catheter 100 can transmit to the motor controller 1212, and the motor controller 1212 can transmit to the motion planning module 1208, information about the actual current position, velocity and torque of the catheter 100 as well as various image space control inputs 124 at the same time the medical image 804 is being formatted and transmitted to the motion planning module 1208. The motion planning module 1208, with the estimated medical image catheter pose and actual pose of the catheter 100 can transmit target position and target peak velocity information to the motor controller 1210, which can transfer that information to the handle 102 of the catheter 100 to actuate the desired change in position of the catheter 100.

FIGS. 13A-18B provide various example embodiments of a steerable catheter system configured for image space control. These embodiments illustrate that the system can be provided in various form factors that facilitate user comfort and control. These are provided by way of example only.

FIGS. 13A-13D illustrate various views of an embodiment a steerable catheter system 1300 configured for image space control. In this example, the handle is provided with an orientation that aligns a longitudinal axis of the handle with the longitudinal axis of the catheter.

Figure 14B:
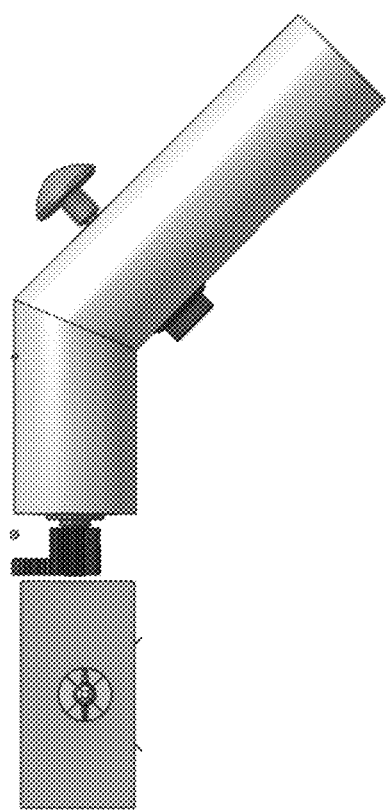
FIGS. 14A-14B illustrate various views of another embodiment a steerable catheter system configured for image space control.
Figure 14A:
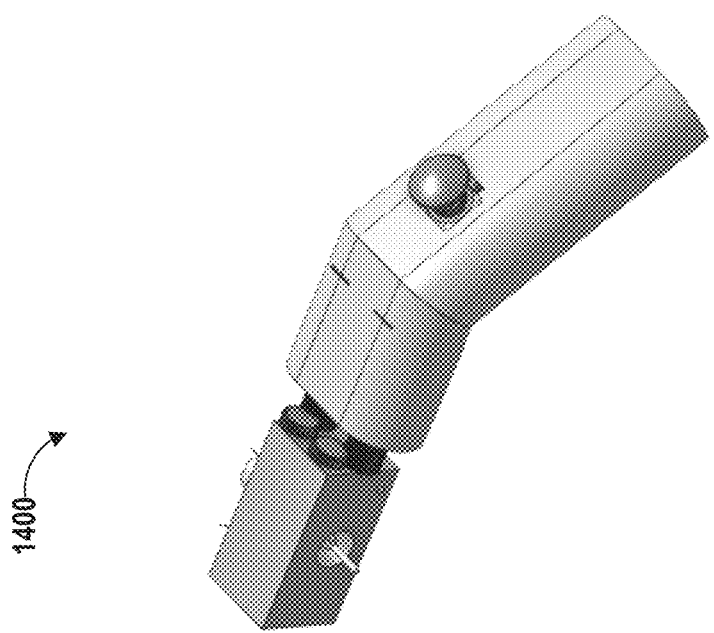

FIGS. 14A-14B illustrate various views of another embodiment a steerable catheter system 1400 configured for image space control. In this example, the handle is provided at a 45-degree angle with respect an axis that is orthogonal with respect to the axis of the catheter.

Figure 15B:
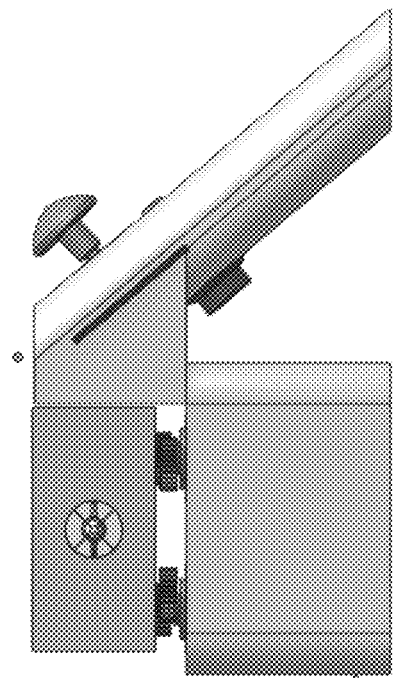
FIGS. 15A-15B illustrate various views of another embodiment a steerable catheter system configured for image space control.
Figure 15A:
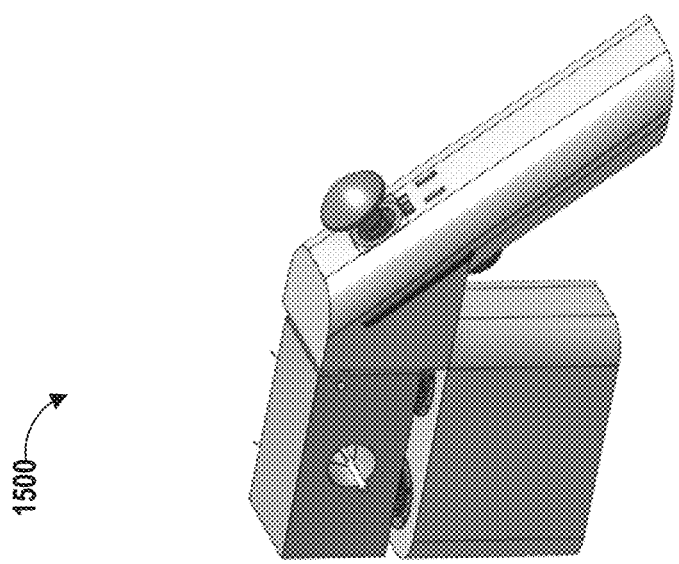

FIGS. 15A-15B illustrate various views of another embodiment a steerable catheter system 1500 configured for image space control. This embodiment is similar to FIGS. 13A-13B but provides an alternative orientation of the motors.

Figure 16B:
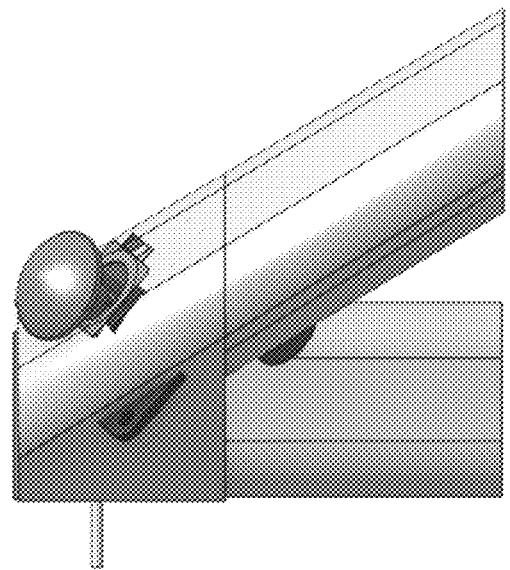
FIGS. 16A-16C illustrate various views of another embodiment a steerable catheter system configured for image space control.
Figure 16A:
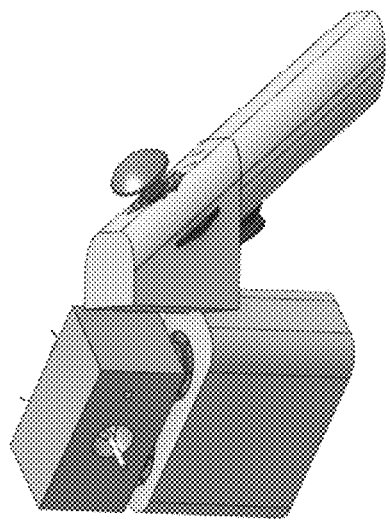
Figure 16C:
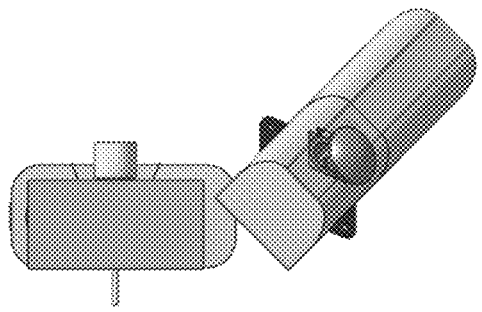

FIGS. 16A-16C illustrate various views of another embodiment a steerable catheter system 1600 configured for image space control. This embodiment is similar to FIGS. 14A-14B but further angles the handle back at another 45-degree angle.

Figure 17A:
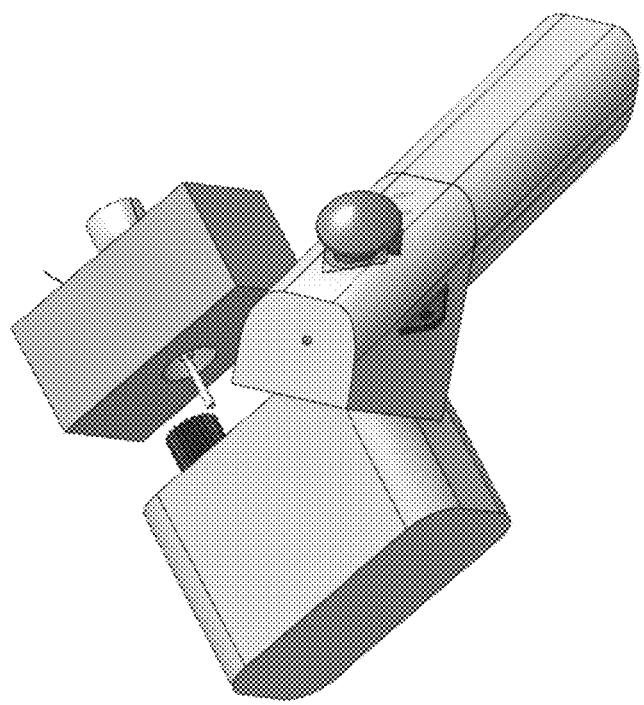
FIGS. 17A-17B illustrate various views of another embodiment a steerable catheter system configured for image space control.
Figure 17B:
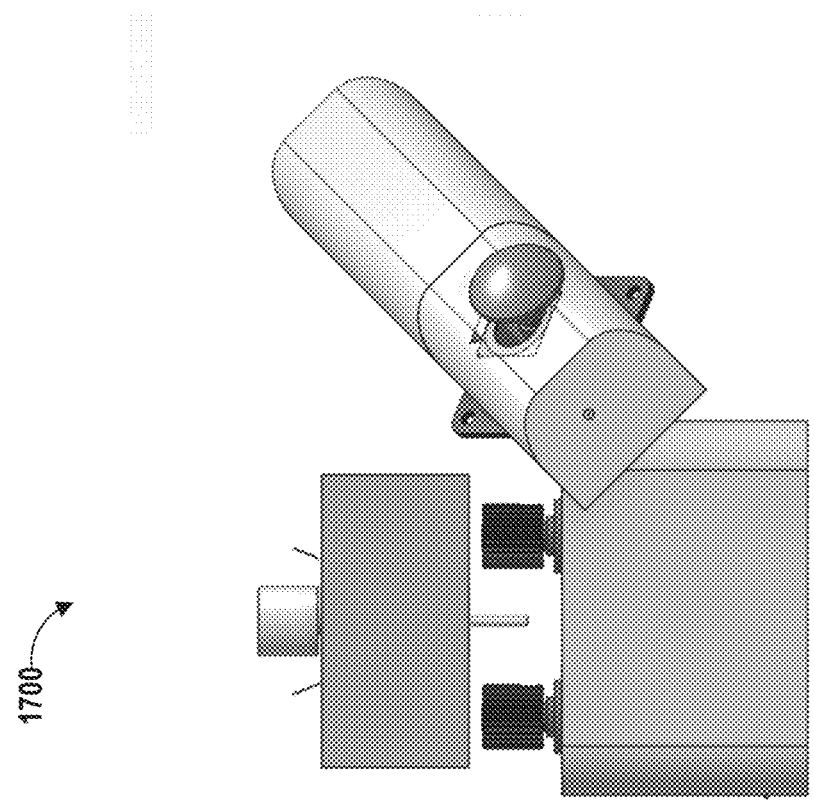

FIGS. 17A-17B illustrate various views of another embodiment a steerable catheter system 1700 configured for image space control. This embodiment is similar to FIGS. 15A-15C but provides an alternative orientation of the motors.

Figure 18B:
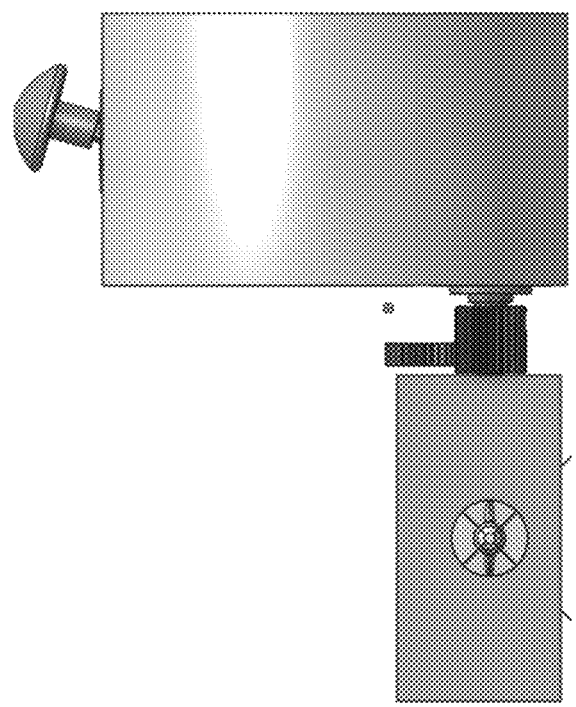
FIGS. 18A-18B illustrate various views of another embodiment a steerable catheter system configured for image space control.
Figure 18A:
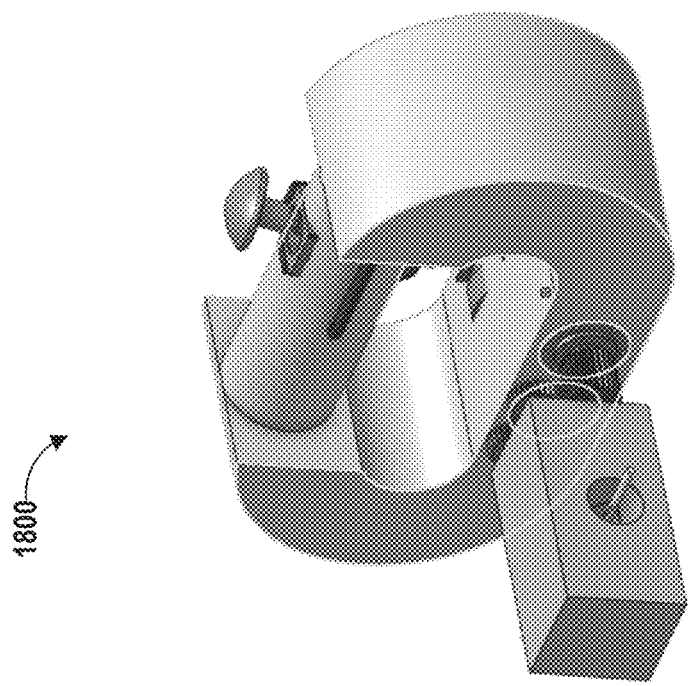

FIGS. 18A-18B illustrate various views of another embodiment a steerable catheter system 1800 configured for image space control. In this example, the handle is oriented to be parallel with axis of the catheter.

The catheters described herein could be used in any procedure performed under x-ray guidance, such as endovascular procedures and others. In some embodiments, no draping would be required for setup, which would proceed in a similar fashion to that of a diathermy. For example, a procedure could include one or more of the following steps: (1) nursing staff open the sterilized, non-consumable handle; (2) the surgeon throws the cord off to be plugged in outside of the sterile field; (3) nursing staff open sterilized, single use reel; (4) surgeon clips reel into handle; and (5) using the handle, the surgeon performs the procedure under X-ray guidance. In some embodiments, at the end of the procedure the reel is disposed of with other single use tools and the reusable handle is sent for sterilization.

The various technologies disclosed herein related to determination of position and/or orientation determination can be used to facilitate the treatment of various diseases and other conditions where a robotic or manual device is advanced through an intraluminal (e.g., intravascular) network of a subject to reach the site of intravascular pathology (e.g., thrombosis, embolus, occlusion, aneurysm, rupture, bleeding, dissection, etc.). In some embodiments, the systems, devices, and methods described herein can be used to facilitate one or more endovascular purposes, surgeries, and/or treatments. For example, in some embodiments, the systems, processes, and methods described herein can be used for one or more of removal of intravascular blockage/reestablishment of perfusion; treatment of vessel wall injury (aneurysm and/or dissection); treatment of bleeding: aneurysm rupture/trauma; and/or the like. Moreover, in some embodiments, the systems, devices, and methods described herein can be used to treat vascular trauma.

In some embodiments, the systems, devices, and methods described herein can be used to facilitate neurovascular applications and/or treatments, such as for example to treat subarachnoid hemorrhage, aneurysm, arteriovenous malformation, and/or the like. In some embodiments, the systems, devices, and methods described herein can be used for cardiovascular applications and/or treatments, such as for example to treat myocardial infarction, coronary artery disease, pacemaker insertion, and/or the like. In some embodiments, the systems, devices, and methods described herein can be used for aortic applications and/or treatments, such as for example to treat aortic dissection, aortic aneurysm, and/or the like. In some embodiments, the systems, devices, and methods described herein can be used for peripheral emboli applications and/or treatments. In some embodiments, the systems, devices, and methods described herein can be used for vascular trauma applications and/or treatments. In some embodiments, the systems, devices, and methods described herein can be used for venous applications and/or treatments.

While the features of this application have largely been described in the context of endoluminal or endovascular procedures, the inventions described herein may also be practiced fluoroscopically guided procedures, such as endoscopic retrograde cholangiopancreatography (ERCP), discography and vertebroplasty, orthopedic and podiatric surgery, urological procedures including pyelography, intracardiac placement of intracardiac devices, ablations, and lumbar punctures.

Figure 19:
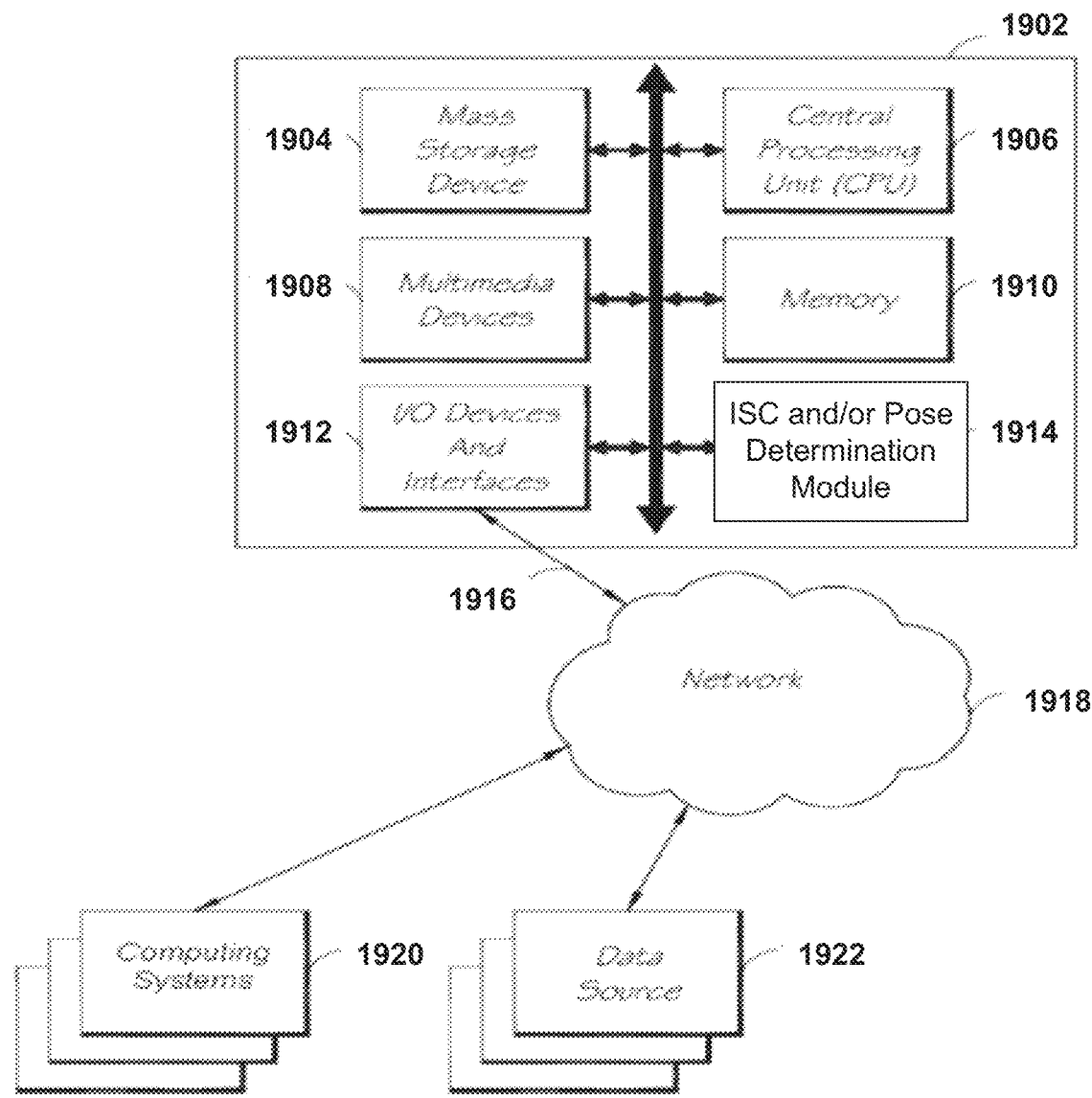
FIG. 19 illustrates an example computer system configured to facilitate and or implement features described herein.

In some embodiments, the systems, processes, and methods described herein are implemented using a computing system, such as the one illustrated in FIG. 19 The example computer system 1902 is in communication with one or more computing systems 1920 and/or one or more data sources 1922 via one or more networks 1918. While FIG. 19 illustrates an embodiment of a computing system 1902, it is recognized that the functionality provided for in the components and modules of computer system 1902 can be combined into fewer components and modules, or further separated into additional components and modules.

The computer system 1902 can comprise an image space control and/or pose determination module 1914 that carries out the functions, methods, acts, and/or processes described herein. The module 1914 is executed on the computer system 1902 by a central processing unit 1906 discussed further below.

In general the word "module," as used herein, refers to logic embodied in hardware or firmware or to a collection of software instructions, having entry and exit points. Modules are written in a program language, such as JAVA, C, C++, and/or the like. Software modules can be compiled or linked into an executable program, installed in a dynamic link library, or can be written in an interpreted language such as BASIC, PERL, LAU, PHP, or Python and/or any such languages. Software modules can be called from other modules or from themselves, and/or can be invoked in response to detected events or interruptions. Modules implemented in hardware include connected logic units such as gates and flip-flops, and/or can include programmable units, such as programmable gate arrays and/or processors.

Generally, the modules described herein refer to logical modules that can be combined with other modules or divided into sub-modules despite their physical organization or storage. The modules are executed by one or more computing systems and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1902 includes one or more processing units (CPU) 1906, which can comprise a microprocessor. The computer system 1902 further includes a physical memory 1910, such as random access memory (RAM) for temporary storage of information, a read only memory (ROM) for permanent storage of information, and a mass storage device 1904, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1902 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1902 includes one or more input/output (I/O) devices and interfaces 1912, such as a keyboard, mouse, touch pad, and printer. The I/O devices and interfaces 1912 can include one or more display devices, such as a monitor, which allows the visual presentation of data to a user. More particularly, a display device provides for the presentation of GUIs as application software data, and multi-media presentations, for example. The I/O devices and interfaces 1912 can also provide a communications interface to various external devices. The computer system 1902 can comprise one or more multi-media devices 1008, such as speakers, video cards, graphics accelerators, and microphones, for example.

The computer system 1902 can run on a variety of computing devices, such as a server, a Windows server, a Structure Query Language server, a Unix Server, a personal computer, a laptop computer, and so forth. In other embodiments, the computer system 1902 can run on a cluster computer system, a mainframe computer system and/or other computing system suitable for controlling and/or communicating with large databases, performing high volume transaction processing, and generating reports from large databases. The computing system 1902 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1902 illustrated in FIG. 19 is coupled to a network 1918, such as a LAN, WAN, or the Internet via a communication link 1016 (wired, wireless, or a combination thereof). Network 1918 communicates with various computing devices and/or other electronic devices. Network 1918 is communicating with one or more computing systems 1920 and one or more data sources 1922. The image space control and/or pose determination module 1914 can access or can be accessed by computing systems 1920 and/or data sources 1922 through a web-enabled user access point. Connections can be a direct physical connection, a virtual connection, and other connection type. The web-enabled user access point can comprise a browser module that uses text, graphics, audio, video, and other media to present data and to allow interaction with data via the network 1018.

The output module can be implemented as a combination of an all-points addressable display such as a cathode ray tube (CRT), a liquid crystal display (LCD), a plasma display, or other types and/or combinations of displays. The output module can be implemented to communicate with input devices 1912 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

The computing system 1902 can include one or more internal and/or external data sources (for example, data sources 1922). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1902 can also access one or more databases 1922. The databases 1922 can be stored in a database or data repository. The computer system 1902 can access the one or more databases 1922 through a network 1918 or can directly access the database or data repository through I/O devices and interfaces 1912. The data repository storing the one or more databases 1922 can reside within the computer system 1902.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Doman Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

It will now be evident to those skilled in the art that there has been described herein methods, systems, and devices for improved routing of catheters and other devices to targeted anatomical locations using robotically controlled assemblies. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary, it is intended to cover any and all equivalents that may be employed without departing from the spirit and scope of the inventions.

While the disclosure has been described with reference to certain embodiments, it will be understood that various changes may be made, and equivalents may be substituted for elements thereof without departing from the scope of the disclosure. In addition, many modifications will be appreciated to adapt a particular instrument, situation, or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A manually-controlled steerable catheter system configured for image space control, the system comprising:
   a manually-controlled steerable catheter comprising:
      a handle configured to be held by a hand of a user, and
      a steerable elongated body extending from the handle and configured for insertion into a lumen of a patient,
      wherein the handle comprises one or more user inputs configured to allow a user to provide image space control commands for articulating the elongated body with respect to a plane of a medical image that includes a view of a distal portion of the elongated body,
      wherein the elongated body comprises one or more pose determination features configured to allow determination of at least a roll angle of the distal portion of the elongated body; and
   a control unit in communication with the manually-controlled steerable catheter, the control unit comprising a processor and a memory storing instructions that configure the processor to:
      receive the image space control commands;
      determine the roll angle of the distal portion of the elongated body based on the one or more pose determination features;
      translate the image space control commands into pullwire commands based on the roll angle; and
      transmit the pullwire commands to the manually-controlled steerable catheter, whereby the elongated body is articulated according to the pullwire commands.

2. The system of claim 1, wherein the one or more pose determination features comprise one or more radio-opaque fiducials positioned on the distal portion of the elongated body, wherein the one or more radio-opaque fiducials are configured such that the roll angle of the distal portion of the elongated body can be determined from the two-dimensional appearance of the one or more radio-opaque fiducials in a medical image that includes a view of the distal portion of the elongated body.

3. The system of claim 1, wherein the one or more pose determination features comprise one or more of: an electromagnetic sensor or a Fiber Bragg grating sensor, and wherein the processor is configured to determine the roll angle based on an output of the an electromagnetic sensor or a Fiber Bragg grating sensor.

4. The system of claim 1, further comprising:
   a medical imager configured to capture the medical image; and
   a display configured to display the medical image to the user.

5. The system of claim 1, wherein the steerable catheter comprises a plurality of pullwires configured for articulation of the distal portion of the elongated body.

6. The system of claim 1, wherein the image space control commands allow a user to provide:
   an in-plane input command to adjust a heading of the steerable catheter within a plane of a medical image; and
   an out-of-plane input command to adjust an incline of the steerable catheter into or out of the plane of the medical image.

7. The system of claim 2, wherein the processor is configured to analyze the medical image to determine the roll angle.

8. The system of claim 5, wherein the plurality of pullwires comprise four pullwires configured to allow deflection of the distal portion of the elongated body in four orthogonal directions.

* * * * *

UNITED STATES PATENT AND TRADEMARK OFFICE
CERTIFICATE OF CORRECTION

PATENT NO. : 12,296,117 B2
APPLICATION NO. : 18/806404
DATED : May 13, 2025
INVENTOR(S) : Sganga et al.

It is certified that error appears in the above-identified patent and that said Letters Patent is hereby corrected as shown below:

In the Specification

Column 2, Line 34, delete "a patient. The" and insert -- a patient, the --.

Column 3, Line 53, delete "of the an electromagnetic" and insert -- of an electromagnetic --.

Column 6, Line 48, delete "facilitate and or implement" and insert -- facilitate and/or implement --.

Column 7, Line 34, delete "including case of" and insert -- including ease of --.

Signed and Sealed this
Eighth Day of July, 2025

Coke Morgan Stewart
*Acting Director of the United States Patent and Trademark Office*